Figure 9:
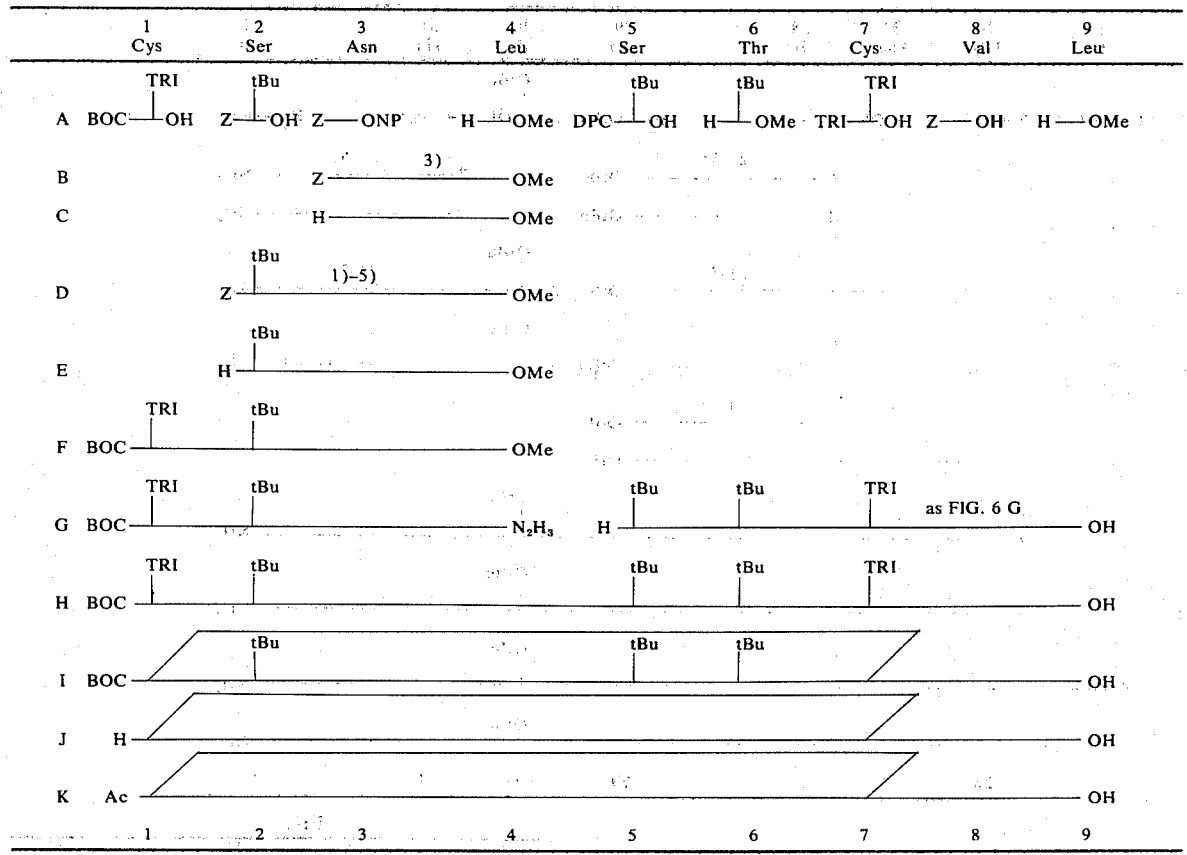
Figure 10:
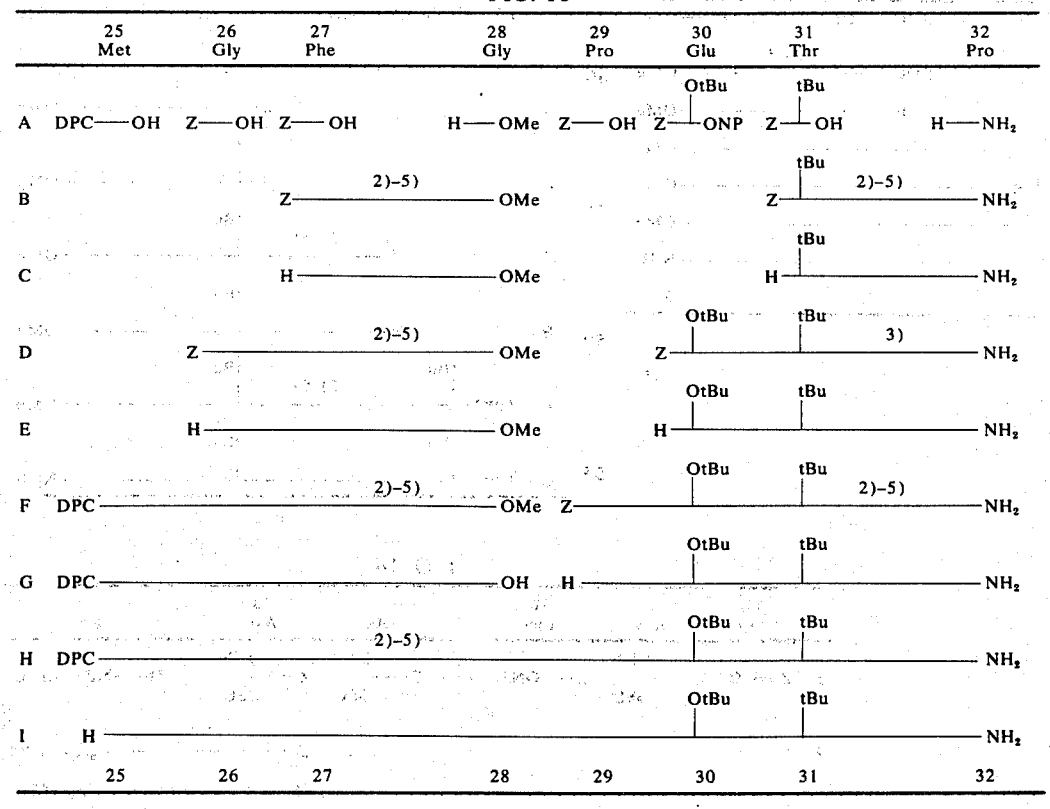

United States Patent [19]
Brugger et al.

[11] 3,956,260
[45] May 11, 1976

[54] HYPOCALCAEMIC PEPTIDES AND PROCESSES FOR THEIR MANUFACTURE

[75] Inventors: Max Brugger, Birsfelden; Friedrich Werner Kahnt; Bruno Kamber, both of Basel; Robert Neher, Binningen; Bernhard Riniker, Frenkendorf; Werner Rittel, Basel; Peter Sieber, Reinach, Basel-Land; Herbert Zuber, Zurich, Glattbrugg, all of Switzerland; Hendrik Marie Greven, Heesch, Netherlands

[73] Assignee: Ciba-Geigy Corporation, Ardsley, N.Y.

[22] Filed: Dec. 10, 1971

[21] Appl. No.: 206,933

Related U.S. Application Data

[63] Continuation of Ser. No. 773,472, Nov. 5, 1968, abandoned.

[30] Foreign Application Priority Data

| Nov. 9, 1967 | Switzerland | 15661/67 |
| Feb. 6, 1968 | Switzerland | 1763/68 |
| Apr. 29, 1968 | Switzerland | 6347/68 |
| May 4, 1968 | Switzerland | 6666/68 |
| May 10, 1968 | Switzerland | 6669/68 |
| May 21, 1968 | Switzerland | 7509/68 |

[52] U.S. Cl. .................... 260/112.5 T; 424/177
[51] Int. Cl.$^2$ ................ C07C 103/52; C07G 7/00
[58] Field of Search .................. 260/112.5, 112.5 T

[56] References Cited

UNITED STATES PATENTS

| 3,256,151 | 6/1966 | Copp et al. ............... 260/112.5 |
| 3,446,789 | 5/1969 | Rudinger et al. .......... 260/112.5 |

FOREIGN PATENTS OR APPLICATIONS

| 1,922,562 | 11/1969 | Germany .................. 260/112.5 |

OTHER PUBLICATIONS

Tashjian et al., Endocrinology, 81, 306 (1967).
Putter et al., J. Am. Chem. Soc. 89, 5301 (1967).
Hawker et al.: Fed. Proc. 26, 392 (1967).
Gudmundsson et al.: Proc. Royal Soc. (London), 164B, pp. 460–469, 476 (1966).
Potts et al., Proc. Nat'l. Acad. Sci., 59, 1321 (1968).

*Primary Examiner*—Lewis Gotts
*Assistant Examiner*—Reginald J. Suyat
*Attorney, Agent, or Firm*—Joseph G. Kolodny; John J. Maitner; Theodore O. Groeger

[57] ABSTRACT

Synthetic hypocalcaemic dotriacontapeptide of the formula

H-Cys-Ser-Asn-Leu-Ser--Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-OH and analogues and derivatives, salts and complexes thereof and process for their manufacture.

1 Claim, No Drawings

HYPOCALCAEMIC PEPTIDES AND PROCESSES FOR THEIR MANUFACTURE

CROSS REFERENCE TO RELATED HEADINGS

This application is a continuation of application Ser. No. 773,472 filed Nov. 5, 1968 and now abandoned.

The subject of the invention is the new hypocalcaemically active peptide of formula I

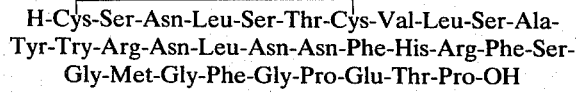
H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-OH

I and corresponding compounds in which one or more of the asparagine residues in positions 3, 15, 17 and 18 are replaced by the aspartic acid residue and/or the glutamic acid residue in positions 30 by the glutamine residue and/or the methionine residue in position 25 by the valine, norvaline, leucine, isoleucine or norleucine residue, as well as acid addition salts, derivatives or complexes of the peptides mentioned, and processes for their manufacture.

As acid addition salts there may especially be quoted salts of therapeutically usable acids such as hydrochloric acid, acetic acid, sulfuric acid, phosphoric acids and sulfonic acids.

As derivatives there may for example be quoted esters, such as lower alkyl esters, for example methyl, ethyl, propyl or tert.-butyl esters and amides, especially the amide which instead of the C-terminal carboxyl group contains the unsubstituted amide group, which is identical with natural porcine thyrocalcitonin, and furthermore the Met$^{25}$-sulphoxide, corresponding $N^\alpha$-acylated peptides and desamino$^1$-peptides.

Acyl groups for the acylation of the $N^\alpha$-amino groups are the residues of carboxylic acids such as aliphatic, aromatic, araliphatic, heterocyclic and heterocyclic-aliphatic carboxylic acids, especially of lower alkane acids such as formic acid, acetic acid, propionic acid and butyric acids, of monocyclic aromatic carboxylic acids such as unsubstituted and substituted benzoic acid, of unsubstituted and aryl-substituted aryl-lower alkylcarboxylic acid such as phenylacetic acid, of 5-membered to 6-membered heterocyclic acids with nitrogen, sulphur and/or oxygen as hetero-atoms, such as pyridinecarboxylic acid, or thiophenecarboxylic acids, or of heterocyclyl-lower alkane acids such as pyridylacetic acid, or imidazolylacetic acid, wherein the substituents of the rings are for example halogen atoms, nitro groups, lower alkyl groups or lower alkoxy groups or lower carbalkoxy groups. Further there may be mentioned as acyl residues, primarily acyl residues of aminoacids, especially α-aminoacids, as for example the pyroglutamyl residue, also acyl residues, which are derived from carbonic acid or thiocarbonic acid or their esters or amides, for example lower alkoxycarbonyl groups, such as ethoxycarbonyl or tert.-butoxycarbonyl, benzyloxycarbonyl groups, carbamoyl and thiocarbamoyl groups, such as N-substituted carbamoyl and thiocarbamoyl groups, for example N-lower alkylcarbamoyl, N-phenylcarbamoyl, or N-phenylthiocarbamoyl groups, in which the aryl residues may be substituted as indicated above.

By complexes there are to be understood the compounds whose structure has not yet been clarified which are produced on adding certain inorganic or organic substances to longchain peptides and which impart a prolonged action to these. Such substances have for example been described for ACTH and other adrenocorticotropically active peptides. There may for example be quoted inorganic compounds which are derived from metals such as calcium, magnesium, aluminum, cobalt and especially zinc, above all sparingly soluble salts such as phosphates, pyrophosphates and polyphosphates as well as hydroxides of these metals, and furthermore alkali metal polyphates, such as for example "Calgon N", "Calgon 322", "Calgon 188" or "Polyron B 12". Organic substances which cause a prolongation of the action are for example non-antigenic gelatines, for example polyhydroxygelatines, polyvinylpyrrolidone and carboxymethylcellulose, and furthermore sulphonic acid or phosphoric acid esters of alginic acid, dextran, polyphenols and polyalcohols, above all polyphloretine phosphate and phytic acid, as well as polymers and copolymers of amino acids, for example protamine or polyglutamic acid.

The new compounds, especially the amide of the compound of formula I, exhibit a hypocalcaemic action. They lower the plasma-calcium and plasma-phosphate content of the blood of mammals, as has been demonstrated by experiments on Wistar rats. Furthermore, they have an inflammation-inhibiting action, as can be demonstrated with kaolin-induced edema on the rat.

The compounds are also effective on human beings. On parenteral administration of 0.01 to 1 mg of the C-terminal amide of the compound of formula I, dissolved in 0.1 M acetate buffer of pH 4.6, serum calcium and serum phosphate diminish. This effect is observed not only in patients suffering from hypercalcaemia, but also in normal-calacemic persons suffering for example, from osteoporosis.

The new compounds may therefore be used for the treatment of hypercalcaemia and of bone diseases such as osteoporosis.

The process according to the invention for the manufacture of the new compounds of formula I and corresponding compounds in which one or more of the asparagine residues are replaced by the aspartic acid residue and/or the glutamic acid residue by the glutamine residue and/or the methionine residue by one of the abovementioned residues, their salts, derivatives and complexes is characterised in that
1. the protective groups are split off from compounds of formula I or the analogues or derivatives mentioned, wherein at least the α-amino group and the terminal and side-chain carboxyl groups are protected, or
2. compounds of formula II H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-OH or the analogues or derivatives mentioned are oxidised to disulphides, or
3. compounds of the formula II or the analogues or derivatives mentioned in which the mercapto groups are protected by the trityl group are oxidized directly to the disulphides, or
4. compounds of formula III or IV

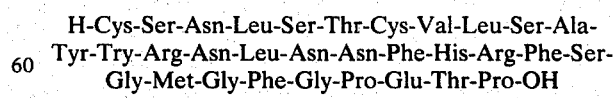

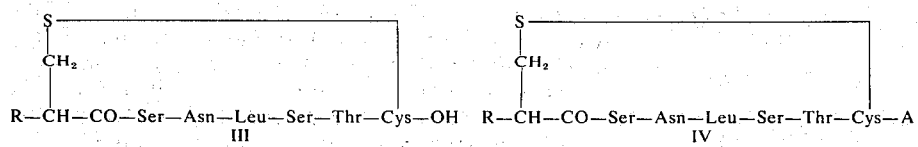

wherein A represents 1 to 21 of the aminoacid residues following the cysteine and R represents hydrogen or an acylated amino group, are condensed with the remaining C-terminal sequence of the peptide (of formula I minus formula III or IV) according to methods known in peptide synthesis, with the proviso that the azide method, the anhydride method or the method of the activated esters is used if the C-terminal sequence exhibits a free carboxyl group, and, if desired, the α-acyl group split off and, if desired, the resulting unsubstituted compounds are converted to their acid addition salts, derivatives or complexes.

In the manufacture of the starting substances for the 1st variant of the process according to the invention as well as of all intermediates required for the four process variants possible protective groups are above all those known from the synthesis of long-chain peptides as well as certain new protective groups which can easily be split off, for example, by hydrolysis, reduction, aminolysis or hydrazinolysis.

Thus for example protective groups used for amino groups are acyl or aralkyl groups such as formyl, trifluoracetyl, phthaloyl, benzenesulphonyl, p-toluenesulphonyl, o-nitrophenylsulphenyl, 2,4-dinitrophenyl, sulfenyl groups (these sulfenyl groups can also be split off by the action of nucleophilic reagents, for example, sulfites, thiosulfates; cf British Patent 1,104,271), benzyl or diphenyl or triphenylmethyl groups which are optionally substituted, for example, by lower alkoxy groups, especially ortho- or paramethoxy groups or groups derived from carbonic acid such as benzyl- or benzhydryloxycarbonyl groups optionally substituted by halogen atoms, such as chlorine or bromine, nitro groups or lower alkoxy groups, for example carbobenzoxy, p-bromocarbobenzoxy, or p-chlorocarbobenzoxy, p-nitrocarbobenzoxy or p-methoxycarbobenzoxy, coloured benzyloxycarbonyl groups such as p-phenylazo-benzyloxycarbonyl and p-(p'-methoxyphenylazo)-benzyloxycarbonyl, aliphatic oxycarbonyl groups such as adamantyloxycarbonyl, cyclopentyloxycarbonyl, trichloroethyloxycarbonyl, tertiary amyloxycarbonyl or above all tert.-butoxycarbonyl, aromatic-aliphatic oxycarbonyl groups such as 2-phenyl-isopropoxycarbonyl, 2-tolyl-isopropoxycarbonyl and especially 2-p-diphenyl-isopropoxycarbonyl (compare Swiss Application G.No. 1073/67 (Case 6106)). The amino groups can also be protected by the formation of enamines obtained by reacting the amino group with 1,3-diketones, for example benzoylacetone, acetylacetone or dimedone.

Carboxyl groups are for example protected by amide or hydrazide formation or by esterification. The amide and hydrazide groups may optionally be substituted, the amide group for example by the 3,4-dimethoxybenzyl or bis-(paramethoxyphenyl)-methyl group, the hydrazide group for example by the carbobenzoxy group, the trichlorethyloxycarbonyl group, the trifluoracetyl group, the trityl group, the tert.-butoxycarbonyl group or the 2-p-diphenyl-isopropoxycarbonyl group. Suitable materials for the esterification are for example lower, optionally substituted alkanols, such as methanol, ethanol, cyanomethyl alcohol, benzoylmethyl alcohol or especially tert.-butanol, also aralkanols such as aryl-lower alkanols, for example benzyl- or benzhydrylalcohols optionally substituted by lower alkyl or lower alkoxy groups or halogen atoms, such as para-nitrobenzylalcohol, para-methoxybenzylalcohol, or 2,4,6-trimethylbenzylalcohol, phenols or thiophenols optionally substituted by electron-attracting substituents, and as thiophenol, thiocresol, para-nitrothiophenol, 2,4,5- or 2,4,6-trichlorophenol, pentachlorophenol, para-nitrophenol, 2,4-dinitrophenol, para-cyanophenol, or para-methanesulfonylphenol, also for example N-hydroxysuccinimide, N-hydroxyphthalimide, N-hydroxypiperidine, 8-hydroxyquinoline.

The hydroxyl groups of the serine, threonine and tyrosine residues may for example by protected by esterification or etherification. In the esterification, acyl residues are for example lower alkanoyl residues, such as acetyl, aroyl residues, such as benzoyl, and in the first place residues derived from carbonic acid, such as benzyloxycarbonyl or ethyloxycarbonyl. Groups suitable for etherification are for example benzyl, tetrahydropyranyl or tertiary butyl residues. Also suitable for the protection of the hydroxyl groups are the 2,2,2-trifluoro-1-tertiary butyloxycarbonylaminoethyl or 2,2,2-trifluoro-1-benzyloxycarbonylaminoethyl group described in Ber. 100 (1967), 3838–3849 (Weygand). However, the hydroxyl groups need not necessarily be protected.

The mercapto groups of the cysteine residues are protected for example by acylation or alkylation. Suitable for the acylation are for example the acetyl or benzoyl residue, the ethyl carbamoyl residue or the optionally substituted carbobenzoxy residue. Suitable for the alkylation are for example the tertiary butyl or benzylthiomethyl residue or optionally substituted arylmethyl groups, such as benzyl, para-nitrobenzyl, diphenylmethyl, dimethoxybenzhydryl or trityl, also phenylcyclohexyl, thienyl (2)-cyclohexyl, etc., cf. Ber. 101, (1968), 681.

Groups used for protecting the amino group in the guanidino grouping of the arginine are above all the nitro group and the tosyl group or the carbobenzoxy group, but the guanidino group does not have to be protected.

Equally, it is not essential for the imino group of the histidine to be protected, but it can be advantageous to protect it, for example by benzyl, trityl, carbobenzoxy, adamantyloxycarbonyl, or the aforementioned Weygand groups.

If the new peptides are synthesised by the Merrifield solid carrier synthesis, the side-chains of serine, threonine and tyrosine may for example by protected by benzyl, those of cysteine by benzyl or p-methoxybenzyl, those of histidine by 1-benzyloxycarbonylamino-2,2,2-trifluorethyl, those of arginine by the nitro group and those of glutamic acid by benzyloxy. Tert.-butoxycarbonyl is for example used as the α-amino protective group. The splitting off of the protected peptide from the resin, and the splitting off of the protective groups, is for example effected with anhydrous hydrogen fluoride.

Preferably, the 1st. variant of the process according to the invention uses the tert.-butoxycarbonyl group for protecting the amino groups, the tert.-butyl ester group for protecting the carboxyl group of the side chain and optionally the terminal carboxyl group, the tert.-butyl ether group for protecting the hydroxyl groups of the serine, threonine and tyrosine residues if the latter are protected at all, and, if desired, the 2,2,2-trifluoro-1-tert.-butoxycarbonyl-aminoethyl group, for the protection of the imino group of the histidine. All these protective groups may, if desired, be split off in one step by acid hydrolysis, for example by means of trifluoracetic acid. In the synthesis of the protected dotriacontapeptide used as starting material in the first variant of the process with the use of protective groups eliminable by means of trifluoracetic acid, the mercapto groups are preferably protected by benzyl or trityl. The S-trityl groups can be eliminated selectively from the protected peptide in organic solution by means of mercuri acetate and hydrogen sulfide (while retaining the groups eliminable with trifluoracetic acid). The S-benzyl groups can be split off selectively from the protected peptide by means of sodium in liquid ammonia. The protected peptide with free mercapto groups is obtained in either case. It can be oxidized to the protected disulfide, for example with iodine in glacial acetic acid, with diiodoethane in an organic solvent, or with atmospheric oxygen in liquid ammonia. It is of particular advantage to protect the mercapto groups by trityl groups, which are then removed from the protected peptide with simultaneous formation of the disulfide bridge with iodine in methanol, cf. Swiss Patent Application No. 6999/68 (Case 6461). Such formation of the disulfide ring can be performed at the stage of a partial sequence containing both cysteine residues, for example at the stage of the nonapeptide 1–9, or at the stage of the dotriacontapeptide.

In the second variant of the process of this invention, the free, open-chained peptide of the formula II used as starting material can also be prepared with the protective groups mentioned for variant I. The S-trityl groups, as all the other protective groups, are advantageously eliminated with trifluoracetic acid. The free, open-chained peptide is oxidized in known manner with potassium ferricyanide in aqueous solution or with iodine or with air in liquid ammonia.

In the third variant of the process the trityl groups are eliminated by the aforementioned procedure with iodine and methanol with simultaneous formation of the disulfide.

In the fourth variant of the process according to the invention active derivatives of the peptides represented in formula I, or of their analogues, namely peptides whose α-amino group is either acylated or missing, are obtained directly. A special α-amino protective group is in this case not necessary. The compounds may however, if desired, by subsequently converted into corresponding peptides with a free α-amino group in a manner which is in itself known, for example by hydrolysis or hydrogenolysis.

The resulting free peptides can subsequently be converted into their acid addition salts, derivatives or complexes in known manner. Thus, in preparing Nα-acyl derivatives the peptide having a free α-amino group can be N-acylated in the usual manner, for example, by reaction with a mixed anhydride or the acid azide containing the acyl residue concerned, primarily with an activated ester, such as the phenyl or a phenyl ester.

The sulfoxide is advantageously prepared by oxidation with dilute hydrogen peroxide solution in a weakly acid medium.

Complexes with inorganic substances, such as sparingly soluble metal compounds, for example aluminium or zinc compounds are prepared in a manner analogous to that known for ACTH, for example by reaction with a soluble salt of the metal concerned, for example zinc chloride or zinc sulfate, and precipitation with an alkali metal phosphate and/or hydroxide. Complexes with organic compounds, such as polyoxy gelatine, carboxymethyl cellulose, polyvinylpyrrolidone, polyphloretine phosphate, polyglutamic acid, etc., are obtained by mixing these substances with the peptide in aqueous solution. In the same manner, insoluble compounds with alkali metal polyphosphates can be prepared.

The peptides used as starting substances are obtained by linking the aminoacids if desired or required with the use of easily eliminable protective groups in the sequence mentioned, either individually or after preliminary formation of smaller peptide units, with the disulphide bridge being optionally formed at a suitable stage of the synthesis. It is appropriate to work in accordance with the linkage methods known from the literature for the manufacture of long-chain peptides taking the disulphide bridge into account.

The linking of the aminoacid and/or peptide units is therefore for example effected by reacting an aminoacid or a peptide with a protected α-amino group and activated terminal carboxyl group with an aminoacid or a peptide with a free α-amino group and free or protected, for example esterified or amidised, terminal carboxyl group, or reacting an aminoacid or a peptide with an activated α-amino group and protected terminal carboxyl group with an aminoacid or a peptide with a free terminal carboxyl group and protected α-amino group. The carboxyl group may for example by activated by conversion into an acid azide, acid anhydride, acid imidazolide, or an activated ester such as cyanomethyl ester, thiophenyl ester, para-nitrothiophenyl ester, thiocresyl ester, para-methanesulfonylphenyl ester, para-nitrophenyl ester, 2,4-dinitrophenyl ester, 2,4,5- or 2,4,6-trichlorophenyl ester, pentachbrophenyl ester, N-hydroxysuccinimide ester, N-hydroxyphthalimide ester, 8-hydroxyquinoline ester or N-hydroxypiperidine ester, or by reaction by means of a carbodiimide (optionally with the addition of N-hydroxysuccinimide) or N,N'-carbonyl-diimidazole or isoxazolium salt, for example Woodward reagent, and the amino group may for example be activated by reaction with a phosphite. As the most common methods there are to be quoted the carbodiimide method, the azide method, the activated ester method and the anhydride method, and also the Merrifield method and the method of the N-carboxy anhydrides or N-thiocarboxy anhydrides.

In addition to the manufacture of the end products, the manufacture of the starting substances, above all of the peptide fragment containing the disulphide bridge, and its linkage to the remaining part of the peptide represents a special subject of the invention. It has been found to be advantageous to start from a sequence which comprises the first 7 - 12 N-terminal aminoacids (1-7, 1-8, 1-9, 1-10, 1-11 or 1-12) and to condense the entire remaining sequence, that is to say 8-32, 9-32, 10-32, 11-32, 12-32, or 13-32 with this N-terminal section. Alternatively, the said N-terminal sequence of the first 7-12 aminoacids may be linked with the fragment up to the 24th aminoacid (glycine) and the tetracosapeptide condensed with the octapeptide of the aminoacids 25-32. The condensation of the said N-terminal fragment with the sequence up to the 32nd or up to the 24th aminoacid is appropriately carried out by the azide method, starting from the azide or hydrazide, or by the method according to Wünsch (carbodiimide in the presence of N-hydroxysuccinimide), starting from the peptide with a free terminal carboxyl group.

In the subsequent text the manufacture of the N-terminal fragment will be explained in more detail in relation to the synthesis of the nonapeptide (1 - 9). The heptapeptide (1 - 7), the octapeptide (1 - 8), the decapeptide (1 - 10), the undecapeptide (1 - 11) and the dodecapeptide (1 - 12) may be manufactured in an entirely analogous manner.

The nonapeptide sequence is, for instance, built up of the sequences 1 - 4 and 5 - 9 or 1 - 6 and 7 - 9, as may be seen from FIGS. 1 – 9; it is however also possible to use other fragments for building up the sequence 1 - 9. The tert.-butoxycarbonyl group or an equivalent group which can be split off by acid hydrolysis is preferably used as the protective group for the α-amino group on the cysteine, or alternatively the corresponding acyl, for example, acetyl, group is used if a $N^\alpha$-acylated dotriacontapeptide is to be manufactured. At the same time it is appropriate to use, as mercapto protective groups, those which can split off selectively relative to the $N^\alpha$-amino protective group (for example the tert.-butoxycarbonyl group) which can be split off by acid hydrolysis, for example the benzyl or trityl group. The terminal carboxyl group of the nonapeptide does not necessarily have to be protected, for example it does not have to be protected if condensations are carried out by the azide or anhydride method (compare for example FIG. 1, columns 5 and 8). These groups may however also be protected by esterification as mentioned above, for example by esterification with methanol (splitting off the ester group with dilute sodium hydroxide solution or conversion to the hydrazide) or with benzyl alcohol or analogues (splitting off the ester group by, for example, hydrogenolysis). The amino groups of the intermediates are protected by means of the usual protective groups, for example carbobenzoxy, trityl, tert.-butoxycarbonyl and above all 2-para-diphenyl-isopropoxycarbonyl. The carboxyl groups of the intermediates are, if necessary, esterified in the usual manner. The hydroxyl groups of the serine residues and of the threonine residue may be protected by etherification, for example with tert.-butanol or equivalents.

In the figures which follow the symbols have the following significance:
1. the azide method
2. the mixed anhydride method
3. the activated ester, especially p-nitrophenyl ester (ONP) or hydroxysuccinimide ester (OSU), method
4. the carbodiimide method
5. the method according to Wünsch

| | |
|---|---|
| BOC | tert.-butoxycarbonyl, |
| DPC | p-diphenyl-isopropoxycarbonyl, |
| Z | carbobenzoxy |
| TRI | trityl |
| Bzl | benzyl |
| NPS | o-nitrophenylsulphenyl |
| OtBu | tert.-butyl ester |

-continued

| | |
|---|---|
| OBzl | benzyl ester |
| ONB | p-nitrobenzyl ester |
| ONP | p-nitrophenyl ester |
| OMe | methyl ester |
| tBu | tert.-butyl ether |
| Ac | acetyl |
| TFA | trifluoracetic acid |

The carbobenzoxy, p-nitrobenzyl ester and benzyl ester groups are split off by hydrogenolysis in the presence of palladium charcoal, the N-trityl group by means of aqueous acetic acid, the tert.-butoxycarbonyl group by means of trifluoracetic acid, the o-nitrophenylsulphenyl group by means of hydrogen chloride in organic solvents or for example by means of prussic acid or sulphurous acid as described in British Patent Specification 1,104,271, and the diphenylisopropoxycarbonyl group by means of, for example, a mixture of glacial acetic acid, formic acid (82.8% strength) and water (7:1:2) as described in Swiss Application G. No. 1073/67 (Case 6106). The p-nitrobenzyl or methyl esters are converted to the hydrazide by means of hydrazine hydrate. The methyl ester group is hydrolysed by means of dilute sodium hydroxide solution. The tert.-butyl ester is split by means of trifluoracetic acid, as is the tert.-butyl ether. The S-trityl groups are removed by means of mercuric acetate and hydrogen sulphide, and the S-benzyl group with sodium in liquid ammonia, with which p-nitrobenzyl ester groups which may possibly be present are split off simultaneously. The ring closure to give the disulphide is for example effected by oxidation with 1,2-diiodoethane.

The C-terminal sequence, comprising the 8th to 13th up to 32nd aminoacid, to be linked to the N-terminal sequence, is preferably composed of the C-terminal fragment 25 - 32 and the sequence up to the 24th aminoacid, that is to say 8 - 24, 9 - 24, 10 - 24, 11 - 24, 12 - 24 or 13 - 24.

Figure 11:
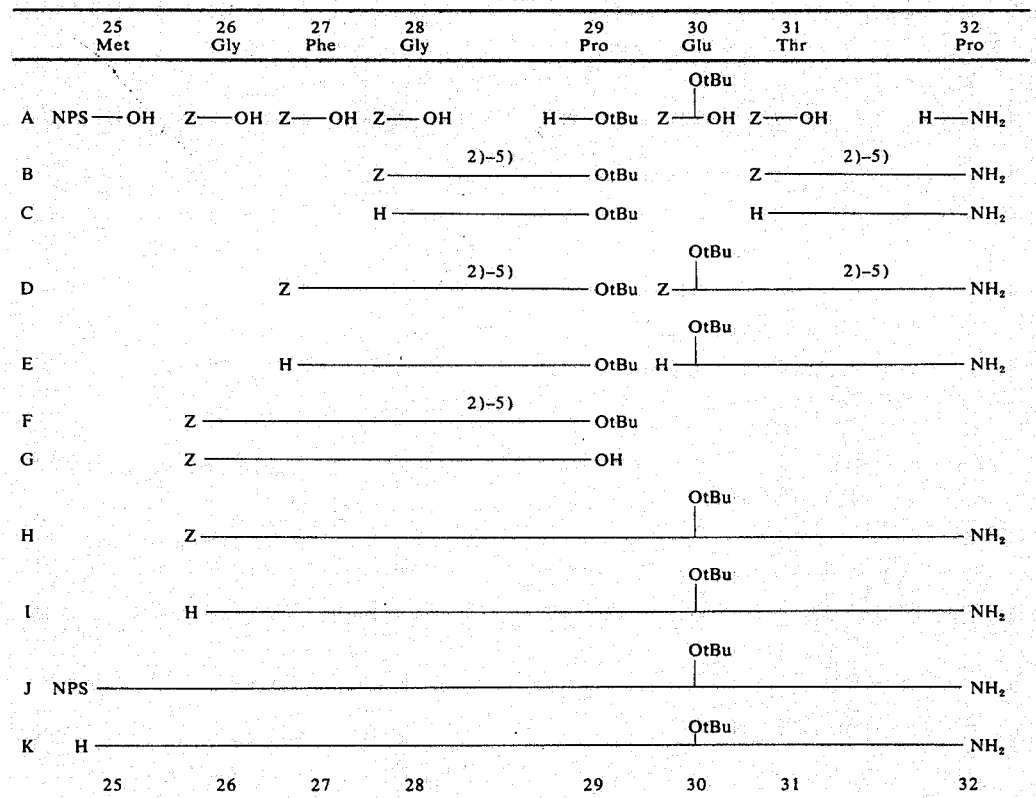
Figure 12:
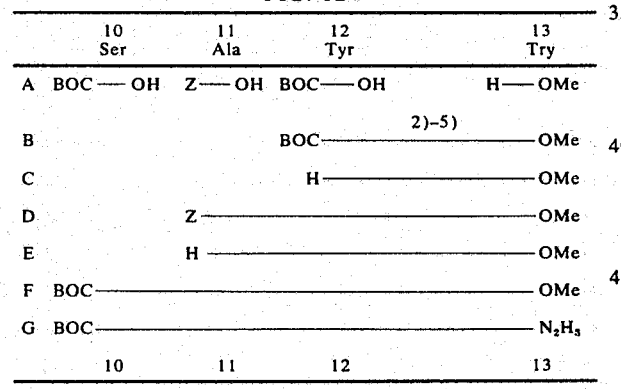

The schematic representation in FIGS. 11 and 12 illustrates the synthesis of the C-terminal octapeptideamide (25 - 32). Preferably, the tripeptide-amide 30 - 32 or the tetrapeptide-amide 29 - 32 is linked by the carbodiimide method to a fragment consisting of the preceding aminoacids.

The γ-carboxyl group of the glutamic acid[30] is appropriately protected by the tert.-butyl ester group. The α-amino protective group DPC is split off with glacial acetic acid-formic acid (82.8 % strength)-water (7:1:2) as mentioned above.

The synthesis of the fragment with the aminoacid sequence of the 8th – 13th up to 24th aminoacid may be effected in various manners. Preferably, the peptide up to the aminoacid in position 13 (tryptophane), i.e. 8 - 13, 9 - 13, 10-13 and so on, is manufactured and this is either condensed with the undecapeptide 14 - 24, or is first condensed with a fragment of this undecapeptide sequence, for example 14 - 16, 14 - 17, 14 - 18 or 14 - 19, and is then linked with the remaining fragment up to aminoacid 24.

Figure 13:
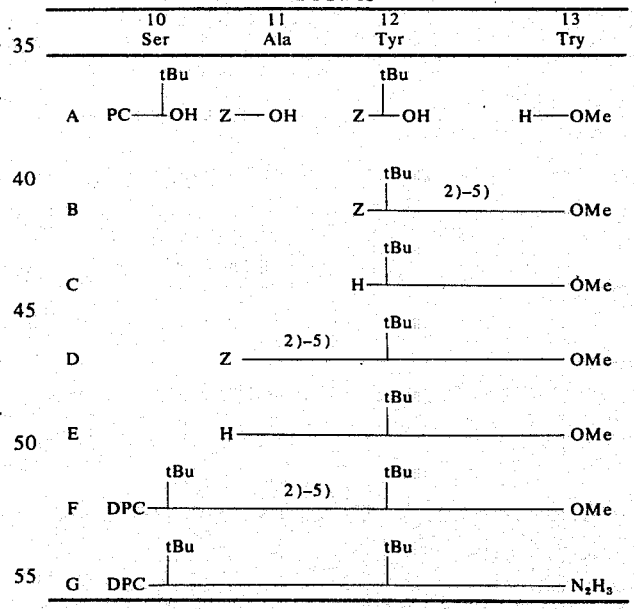
Figure 14:
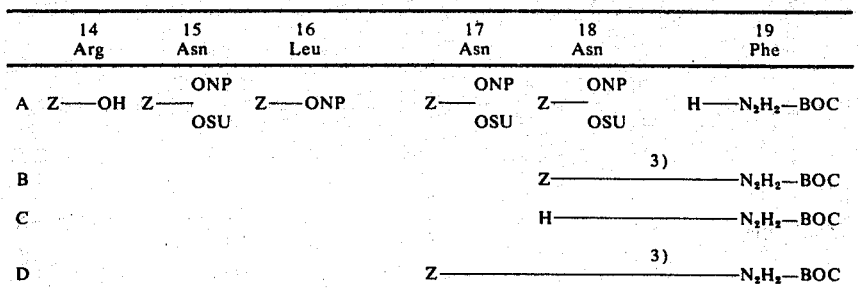

FIGS. 13 and 14 illustrate the synthesis of the tetrapeptide of the 10th. – 13th. aminoacid in the form of the hydrazide, which may be condensed by the azide method with the subsequent aminoacids, for example with the undecapeptide mentioned or with a fragment thereof.

The undecapeptide comprising the sequence 14 - 24 is, according to this invention, preferably built up of the sequences 14 - 19 and 20 - 24 or 14 - 20 and 21 - 24.

Figure 17:
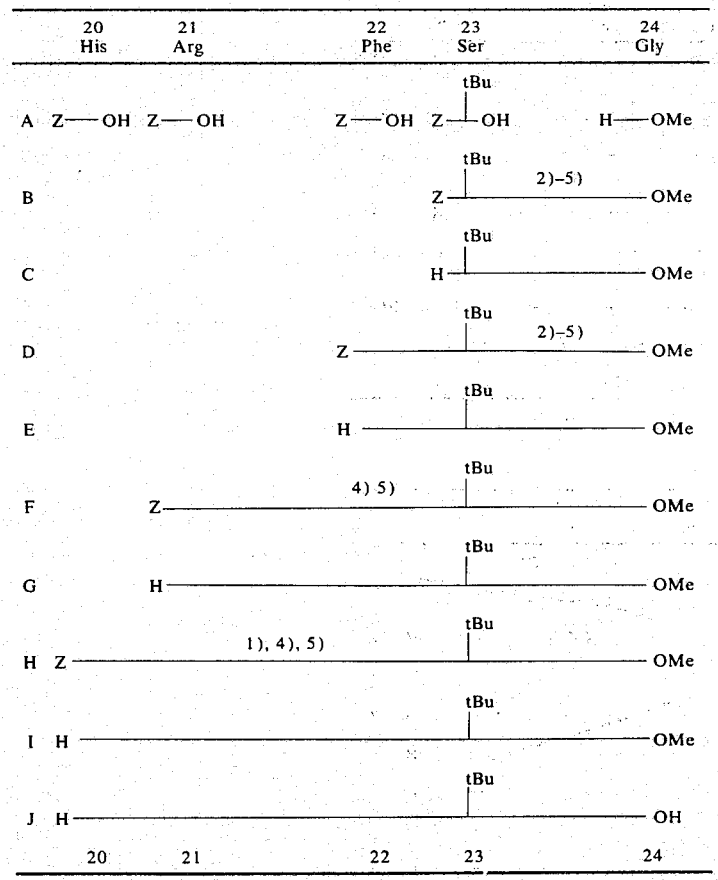
Figure 18:
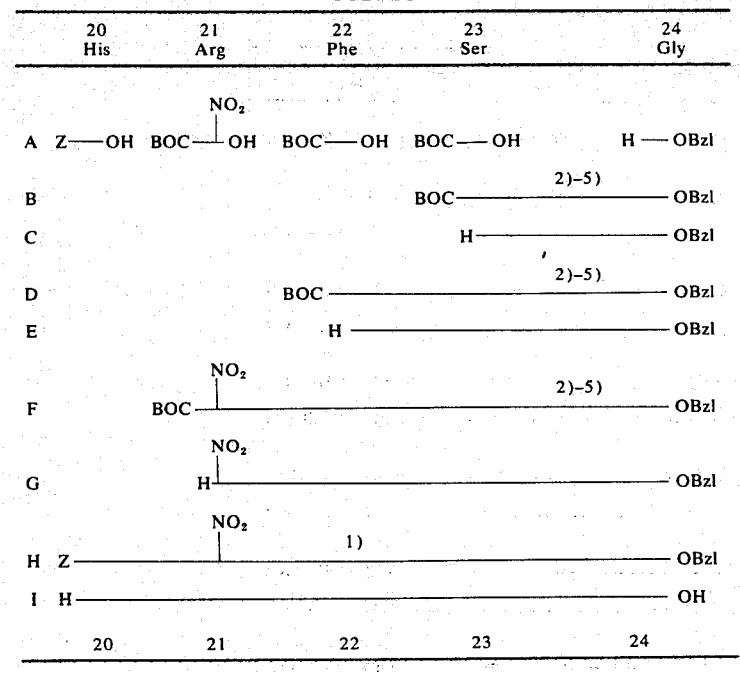

The hexapeptide 14 - 19 or the heptapeptide 14 - 20 are appropriately linked with the remaining sequence up to the 24th. aminoacid by the azide method. FIGS. 15, 16 and 17 illustrate the synthesis of the hexapeptide-hydrazide 14 - 19 and of the heptapeptide-hydrazide 14 - 20. The aminoacid derivative H-His-$N_2H_2$-BOC mentioned in FIG. 17 A is obtained by condensation of Z-His-OH with BOC-NH-$NH_2$ by means of dicyclohexylcarbodiimide in ethyl acetate and hydrogenolytic splitting off of the carbobenzoxy group. The protected phenylalanine-hydrazide in FIGS. 15 A and 16 A is manufactured analogously. The BOC group is split off from the hydrazine residue by means of trifluoracetic acid and the carbobenzoxy group by hydrogenolysis. Instead of the BOC and carbobenzoxy group, equivalent protective groups may be used. FIGS. 18 – 20 illustrate the synthesis of the sequences 20 - 24 and 21 - 24 respectively, which may be linked to the sequence 14 - 19 (in FIG. 16, step J, after hydrogenolytically splitting off the Z group from the hydrazine residue) or the sequence 14 - 20, respectively, to give the undecapeptide 14 - 24.

It is however also possible to link the sequences 14 -19 or 14 - 20, respectively, of FIG. 16 K or of FIGS. 15 J or 17 L, after splitting off the α-amino protective group by hydrogenolysis or by means of trifluoracetic acid, with the sequence 10 - 13 by the azide method to give the sequence 10 - 19 or 10 - 20 respectively, and then to split off the BOC or carbobenzoxy protective group from the protected hydrazide as above and to link the sequence 10 - 19 or 10 - 20, respectively, by the azide method with the sequence 20 - 24 or 21 - 24 respectively to give the pentadecapeptide 10 - 24.

The sequence of the pentadecapeptide 10 - 24, as for example results by joining the fragments represented in FIGS. 13 – 20, may for example by condensed by the method of Wunsch with the octapeptide-amide 25 - 32, as represented in FIGS. 11 or 12, to give the protected tricosapeptide-amide 10 - 32.

It is also possible first to condense the pentadecapeptide 10-24 with the N-terminal sequence 1-9, advantageously in the manner described below for the tricosapeptideamide 10-32, and then to link the tetracosapeptide with the octapeptideamide 25-32, for example according to Wünsch.

A further possibility according to the invention of synthesising the protected tricosapeptide-amide of the aminoacids 10 - 32 consists of linking the sequence 10 - 16, preferably by the azide method, with the sequence 17 - 32. The sequence 10 - 16 may for example be manufactured by condensation of the derivatives of sequence 10 - 13, mentioned in FIGS. 13 or 14, with the tripeptide 14 - 16 (H-Arg-Asn-Leu-OH, for example obtained from Z-Arg-Asn-Leu-OBzl by hydrogenolysis) by the azide method. The sequence 17 - 32 is preferably synthesised from sequences 17 - 24 and 25 - 32 (octapeptide-amide), for example by condensation by the Wünsch method. The octapeptide derivative Asn-Asn-Phe-His-Arg-Phe-Ser-Gly-OH having a protected α-amino group and optionally protected hydroxyl group of the serine residue may for example be obtained by condensation of Z-Asn-Asn-Phe-His-$N_2H_3$ (from FIG. 17 F by means of trifluoracetic acid) with H-Arg-Phe-Ser(tBu)-Gly-OH (FIG. 20 H) by the azide method.

The protective group is removed from the tricosapeptide-amide 10 - 32 having a protected α-amino group in a suitable manner (BOC with trifluoracetic acid, whereby a tert.-butyl ester group on the γ-carboxyl group of glutamic acid[30] and tert.-butyl ether groups which may possibly be present are also hydrolysed; DPC by means of glacial acetic acid - formic acid-water, whereby tert.-butyl ester and tert.-butyl ether groups are not attacked). The linkage of the sequence 1 - 9, which contains the disulphide bridge and in which at least the α-amino group is protected, with the sequence 10 - 32 is, as has already been mentioned, preferably effected by the azide method.

The dotriacontapeptide-amide having a protected α-amino group and optionally protected side chain hydroxyl and/or carboxyl groups is thus obtained. These protective groups are split off in the manner already mentioned.

The dotriacontapeptide with free SH groups to be used for the process according to variant 2 may be manufactured analogously to the protected dotriacontapeptide described above, with the difference that the protected SH groups are retained up to the completion of the synthesis. The SH protective groups are only split off as mentioned above after all other protective groups have been removed from the protected dotriacontapeptide.

The synthesis according to variant 4 of the process is particularly suitable for the manufacture of end products of formula I having an acylated or converted amino group, above all the $N^{\alpha}$ -acetylated compound. The fragment of formula III, compare for example FIG. 9 K, may be manufactured according to the processes illustrated above for the sequence 1 - 9; however it is also possible to choose the acyl group which is to be retained to act as the α-amino protective group from the start. The methods of synthesis correspond to those described above.

Depending on the procedure, the new compounds are obtained in the form of bases or of their salts. The bases may be obtained from the salts in a manner which is in itself known. Salts may again be obtained from the latter by reaction with acids which are suitable for the formation of therapeutically usable salts, such as for example those with inorganic acids, such as hydrogen halide acids, for example hydrochloric acid or hydrobromic acid, perchloric acid, nitric acid or thiocyanic acid, sulphuric or phosphoric acids, or organic acids such as formic acid, acetic acid, propionic acid, glycollic acid, lactic acid, pyruvic acid, oxalic acid, malonic acid, succinic acid, maleic acid, fumaric acid, malic acid, tartaric acid, citric acid, ascorbic acid, hydroxymaleic acid, dihydroxymaleic acid, benzoic acid, phenylacetic acid, 4-aminobenzoic acid, 4-hydroxybenzoic acid, anthranilic acid, cinnamic acid, mandelic acid, salicylic acid, 4-aminosalicylic acid, 2-phenoxybenzoic acid, 2-acetoxybenzoic acid, methanesulphonic acid, ethanesulphonic acid, hydroxyethanesulphonic acid, benzenesulphonic acid, p-toluenesulphonic acid, naphthalenesulphonic acid or sulphanilic acid.

The peptides obtained in accordance with the process may be used in the form of pharmaceutical preparations. These contain the peptides mixed with an organic or inorganic pharmaceutical excipient suitable for enteral or parenteral administration. Possible materials for these are such materials as do not react with the polypeptides, such as for example gelatine, lactose, glucose, common salt, starch, magnesium stearate, talc, vegetable oils, benzyl alcohols, gum, polyalkylene glycols, white petroleum jelly, cholesterol or other known medicinal excipients. The pharmaceutical preparations may for example be in the form of a lyophilisate or in liquid form as solutions, suspensions or emulsions. They are optionally sterilised and/or contain auxiliary substances such as preservatives, stabilisers, wetting agents or emulsifiers. They may further contain other therapeutically valuable substances.

The invention is described in the following examples.

The following systems are used in the thin layer chromatography:

System 43A : tert.-amyl alcohol-isopropanol-water (100:40:10)
System 43C : tert.-amyl alcohol-isopropanol-water (51:21:28)
System 45 : sec. butanol-3% strength aqueous ammonia (70:30)
System 52 : n-butanol-glacial acetic acid-water (75:7.5:21)
System 52A : n-butanol-glacial acetic acid-water (67:10:23)
System 53 : n-butanol-formic acid-water (60:0.75:39)
System 54 : sec. butanol-isopropanol-9% strength monochloracetic acid (58:8:34)
System 55 : ethanol-8% strength aqueous sodium chloride (75:25)
System 59 : methyl ethyl ketone-pyridine-water (60:15:25)
System 70 : ethyl acetate-pyridine-water (40:20:40)
System 89 : ethyl acetate-acetone-water (72:24:4)
System 96 : sec. butanol-glacial acetic acid-water (67:10:23)
System 100 : ethyl acetate-pyridine-glacial acetic acid-water (62:21:6:11)
System 101 : n-butanol-pyridine-glacial acetic acid-water (38:24:8:30)
System 101A : n-butanol-pyridine-glacial acetic acid-water (42:24:4:30)
System 101B : n-butanol-pyridine-glacial acetic acid-water (40:24:6:30)
System 102E : ethyl acetate-methyl ethyl ketone-glacial acetic acid-water (50:30:10:10)
System 104 : chloroform-methanol-17% strength aqueous ammonia (41:41:18)
System 111A : n-butanol-pyridine-ammonia (26% strength)-water (42:24:4:30)
System 121 : isopropanol-ammonia (26% strength)-water (70:10:20)
System 121A : isopropanol-ammonia (26% strength)-water (85:5:10)
System 87 : isopropanol-glacial acetic acid-water (77:4:19)
System 101 : ethyl acetate-n-butanol-pyridine-glacial acetic acid-water (42:21:21:6:10)
System 1 : benzene-ethanol (80:20)
System 2 : benzene-ethanol (90:10)
System 3 : benzene-ethanol (95:5)
System 4 : n-amyl alcohol-formic acid-water (70:20:10)
System 5 : n-butanol-acetic acid-water (66.6:16.7:16.7)
System 6 : n-butanol-pyridine-acetic acid-water (66.6:12.5:4.2:16.7)
System 7 : n-amyl alcohol-pyridine-water (50:30:20)
System 8 : chloroform-methanol-acetic acid (87.4:9.7:2.9)

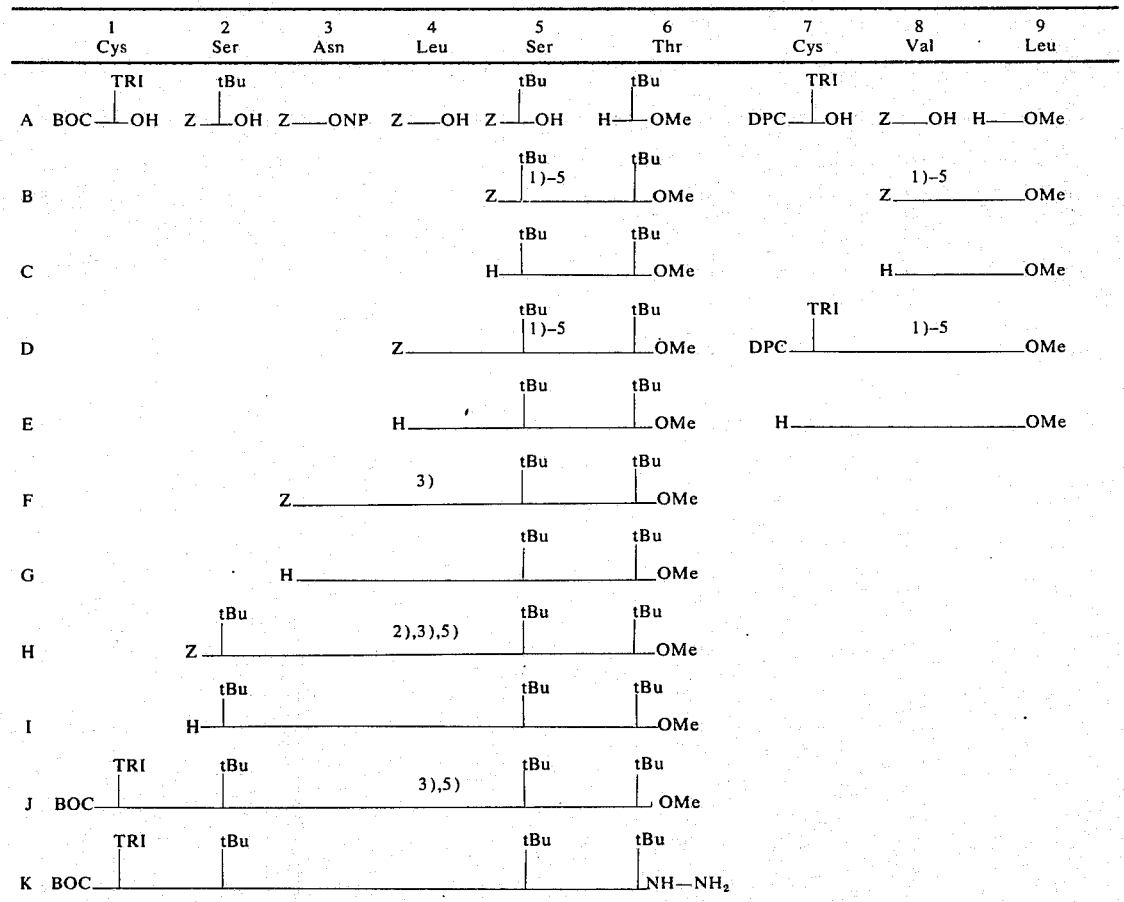

FIG. 1

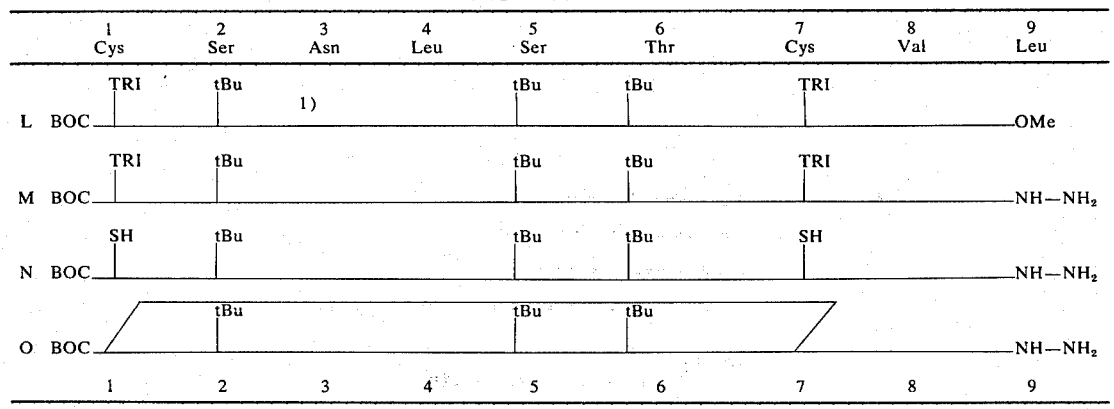
FIG. 1-continued
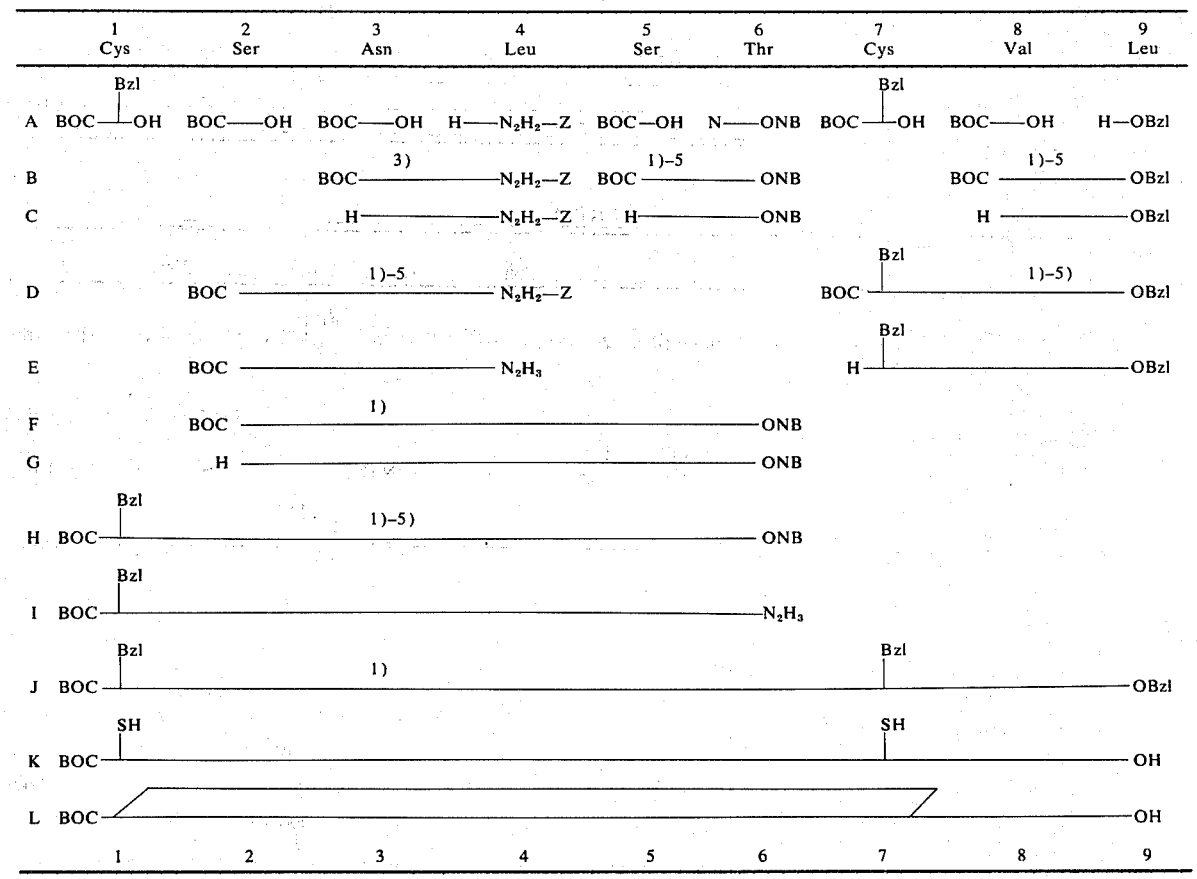
FIG. 2
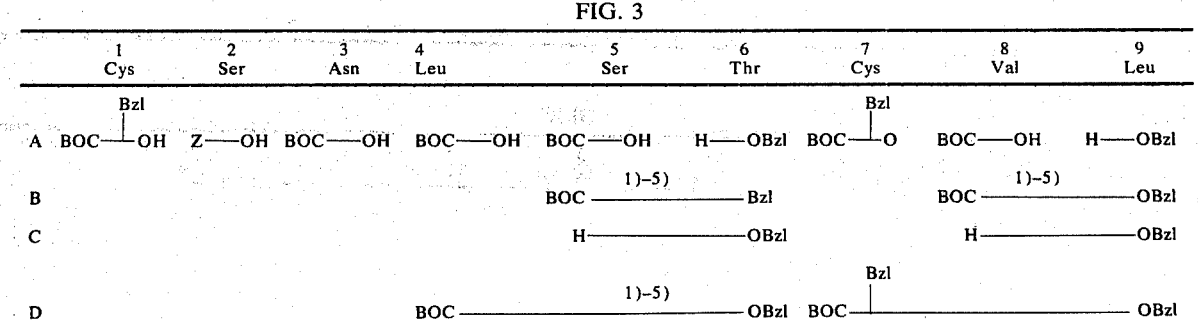
FIG. 3

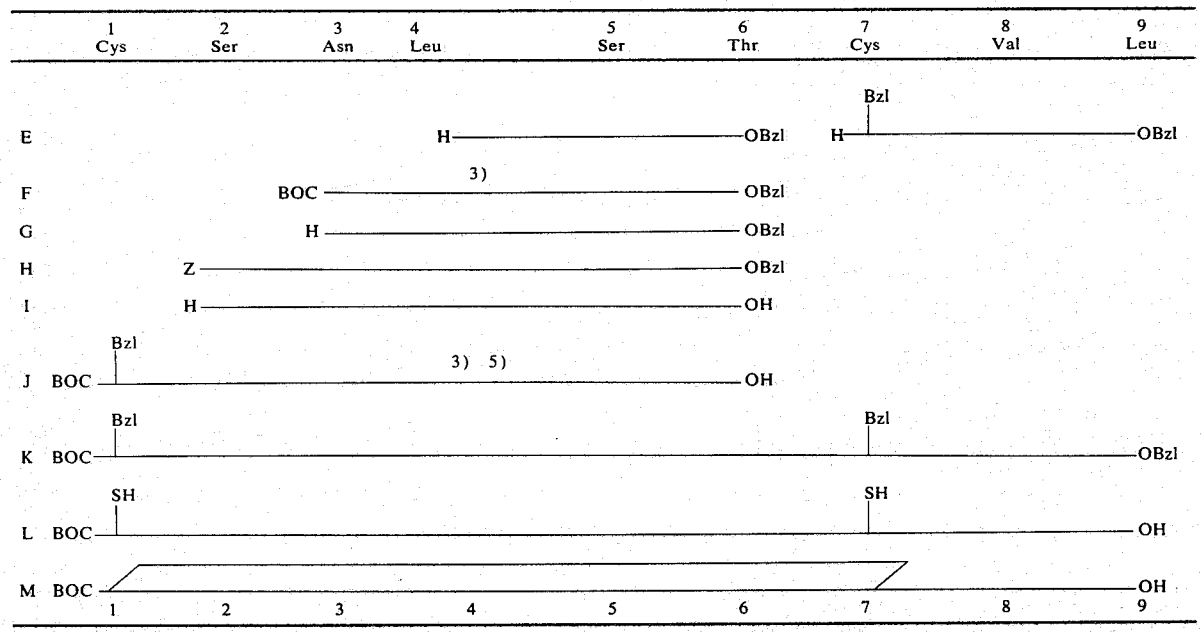
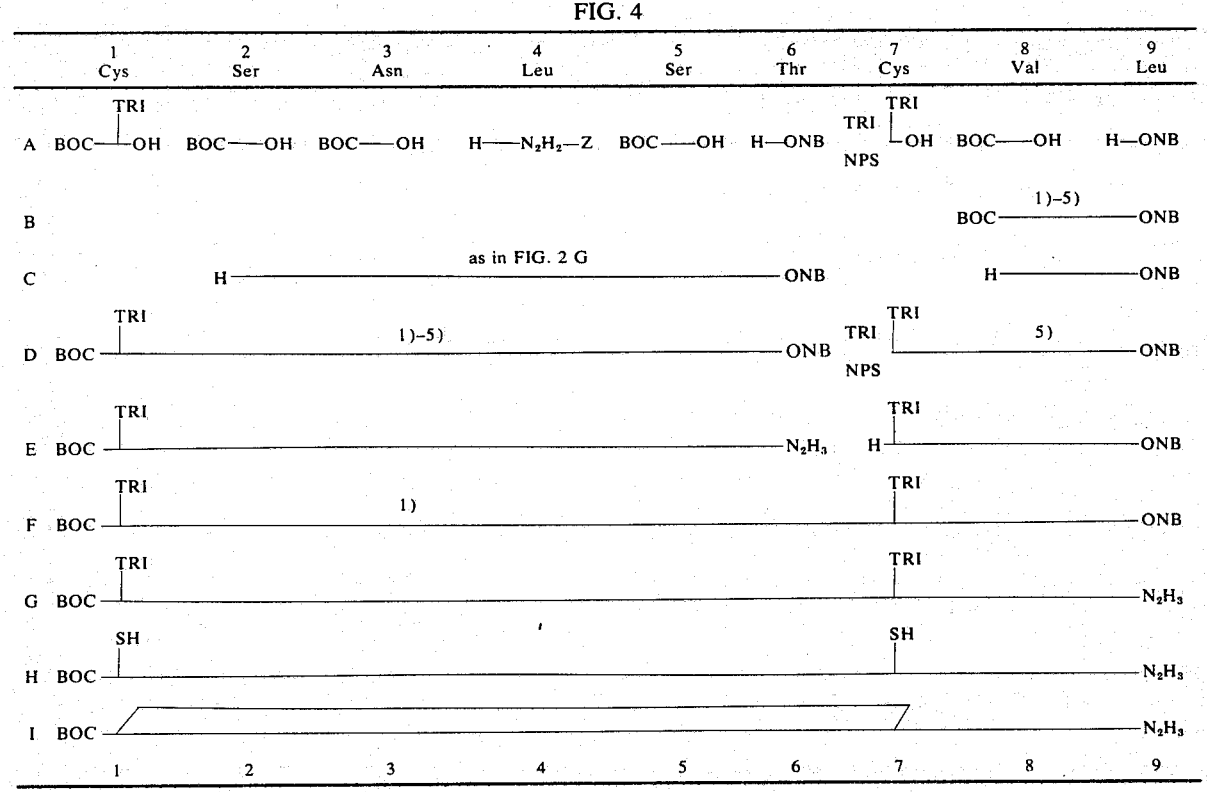
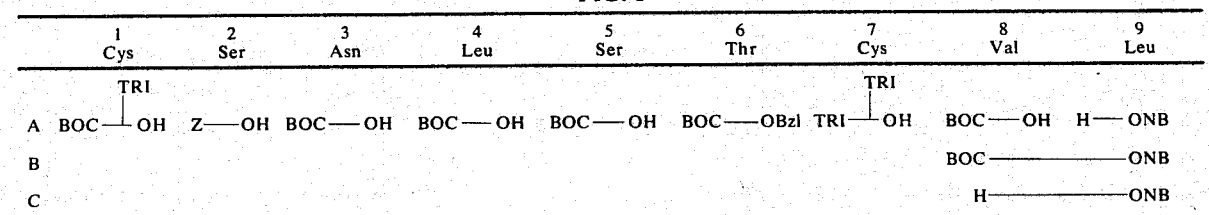

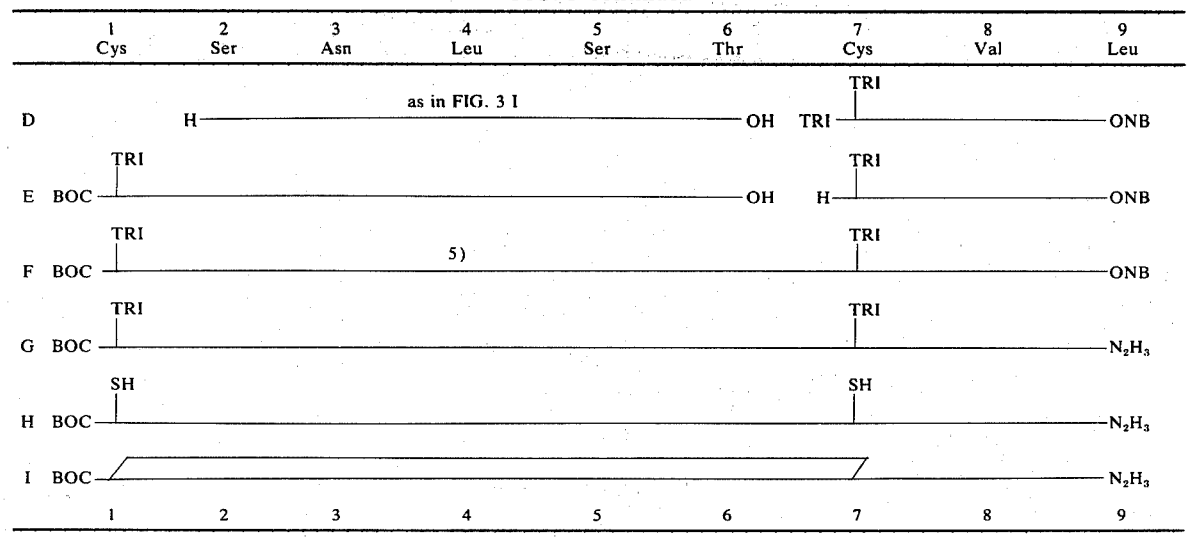
FIG. 5-continued
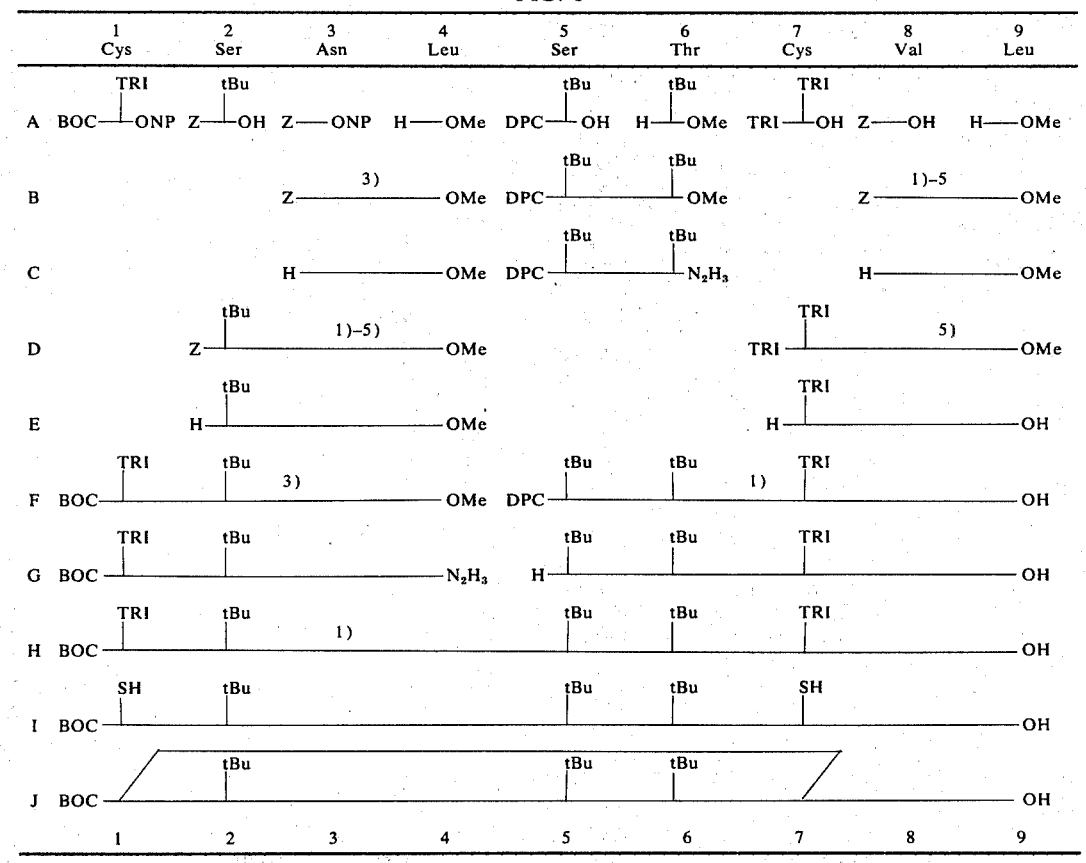
FIG. 6
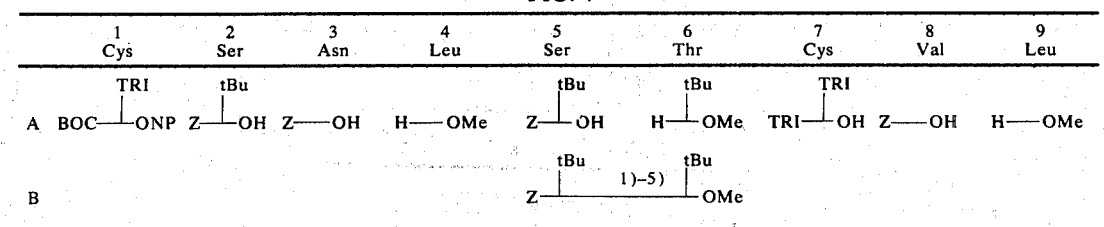
FIG. 7

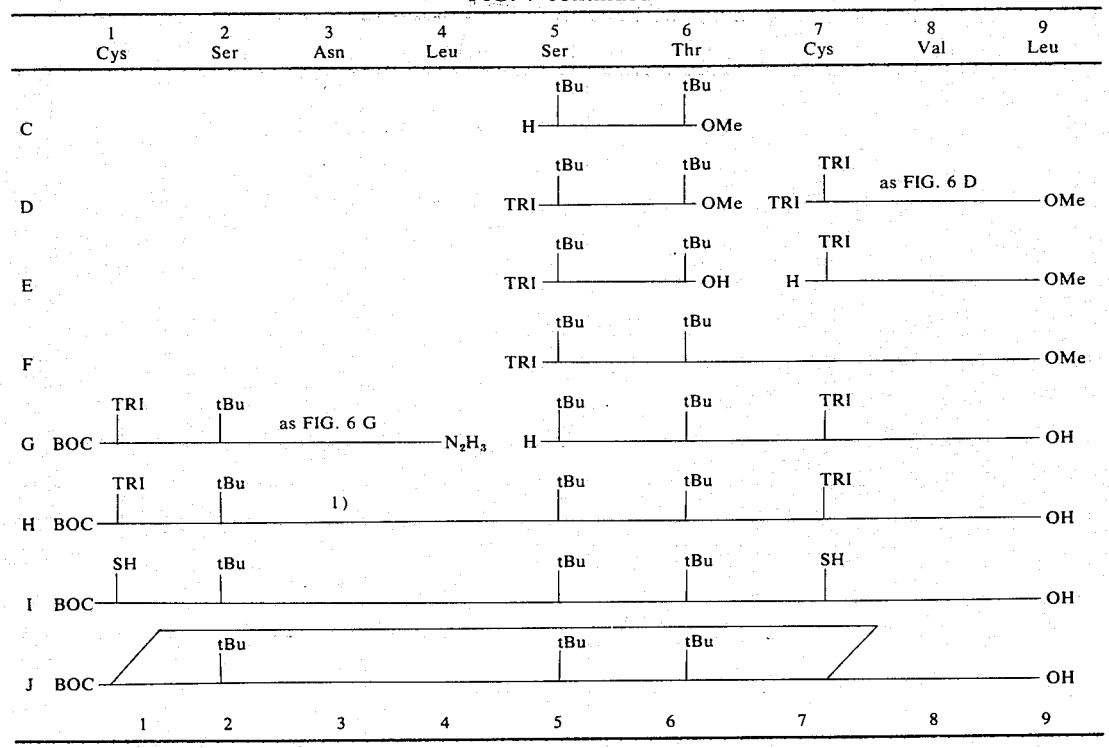
FIG. 7-continued
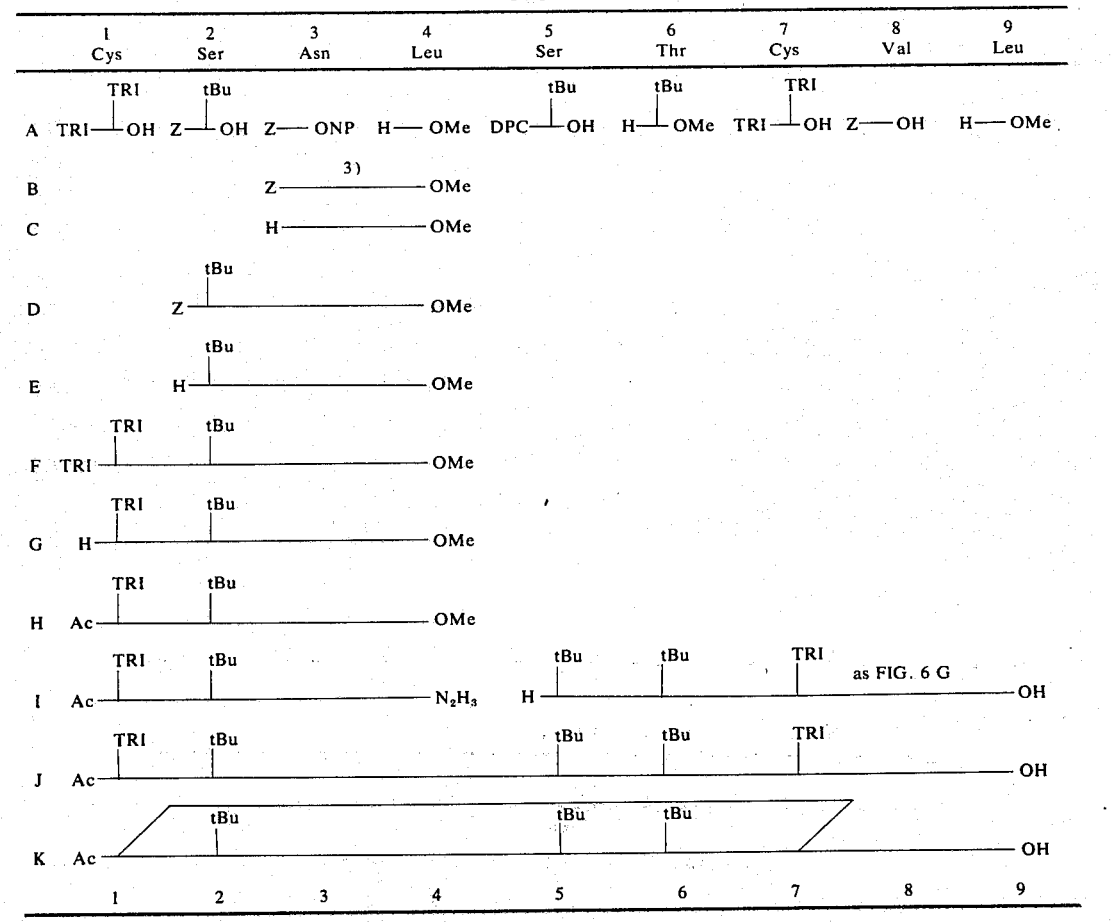
FIG. 8

FIG. 14-continued

| | 14 Arg | 15 Asn | 16 Leu | 17 Asn | 18 Asn | 19 Phe |
|---|---|---|---|---|---|---|
| E | | | | H— | —————— | —$N_2H_2$—BOC |
| F | | Z— | ——————— | ——3)—— | ——————— | —$N_2H_2$—BOC |
| G | | H— | ——————— | ——————— | ——————— | —$N_2H_2$—BOC |
| H | Z— | ——————— | ——————— | ——3)—— | ——————— | —$N_2H_2$—BOC |
| I | H— | ——————— | ——————— | ——————— | ——————— | —$N_2H_2$—BOC |
| J | Z— | ——————— | ——4) 5)—— | ——————— | ——————— | —$N_2H_2$—BOC |
| K | Z— | ——————— | ——————— | ——————— | ——————— | —$N_2H_3$ |
| | 14 | 15 | 16 | 17 | 18 | 19 |

FIG. 15

| | 14 Arg | 15 Asn | 16 Leu | 17 Asn | 18 Asn | 19 Phe |
|---|---|---|---|---|---|---|
| A | BOC——OH | BOC——OH | BOC——OH | BOC——OH | BOC——OH | H——$N_2H_2$—Z |
| B | | | | | BOC———— | —$N_2H_2$—Z |
| C | | | | | H———— | —$N_2H_2$—Z |
| D | | | | BOC———— | ———— | —$N_2H_2$—Z |
| E | | | | H———— | ———— | —$N_2H_2$—Z |
| F | | | BOC———— | ———— | ———— | —$N_2H_2$—Z |
| G | | | H———— | ———— | ———— | —$N_2H_2$—Z |
| H | | BOC———— | ———— | ———— | ———— | —$N_2H_2$—Z |
| I | | H———— | ———— | ———— | ———— | —$N_2H_2$—Z |
| J | BOC———— | ———— | ———— | ———— | ———— | —$N_2H_2$—Z |
| K | H———— | ———— | ———— | ———— | ———— | —$N_2H_2$—Z |
| | 14 | 15 | 16 | 17 | 18 | 19 |

FIG. 16

| | 14 Arg | 15 Asn | 16 Leu | 17 Asn | 18 Asn | 19 Phe | 20 His |
|---|---|---|---|---|---|---|---|
| A | Z——OH | Z——ONP | Z——OH | Z——ONP | Z——ONP | Z——OH | H——NH—NH—BOC |
| B | | | | | | Z——2)-5)—— | —NH—NH—BOC |
| C | | | | | | H———— | —NH—NH—BOC |
| D | | | | | Z——3)—— | ———— | —NH—NH—BOC |
| E | | | | | H———— | ———— | —NH—NH—BOC |
| F | | | | Z——3)—— | ———— | ———— | —NH—NH—BOC |
| G | | | | H———— | ———— | ———— | —NH—NH—BOC |
| H | | | Z——2)-5)—— | ———— | ———— | ———— | —NH—NH—BOC |
| I | | | H———— | ———— | ———— | ———— | —NH—NH—BOC |
| J | | Z——3)—— | ———— | ———— | ———— | ———— | —NH—NH—BOC |
| K | | H———— | ———— | ———— | ———— | ———— | —NH—NH—BOC |
| L | Z——4) 5)—— | ———— | ———— | ———— | ———— | ———— | —NH—NH—BOC |
| M | Z———— | ———— | ———— | ———— | ———— | ———— | —NH—$NH_2$ |
| | 14 | 15 | 16 | 18 | 19 | 20 | |

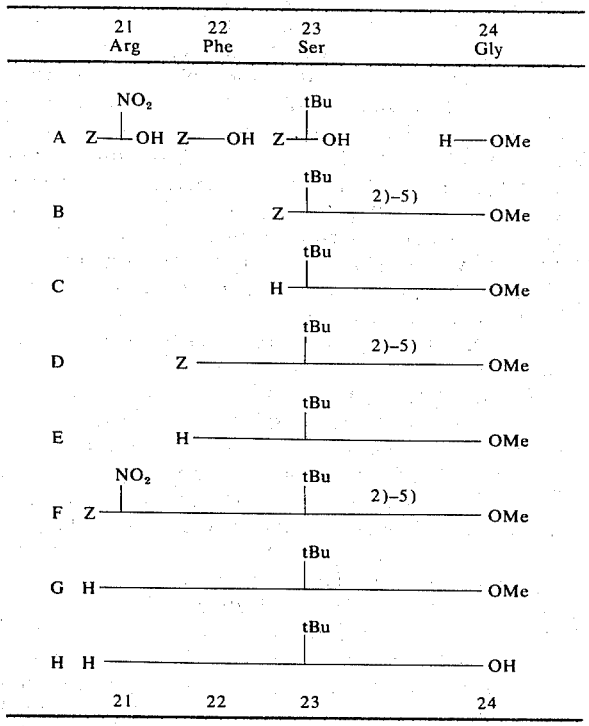

FIG. 19

EXAMPLE 1

H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-NH$_2$ (I, Thyrocalcitonin).

480 mg of BOC-Cys-Ser(tBu)-Asn-Leu-Ser(tBu)-Thr(tBu)-Cys-Val-Leu-Ser(tBu)-Ala-Tyr(tBu)-Try-Arg(H$_2^+$)-Asn-Leu-Asn-Asn-Phe-His-Arg(H$_2^+$)-Phe-Ser(tBu)-Gly-Met-Gly-Phe-Gly-Pro-Glu(OtBu)-Thr(tBu)-Pro-NH$_2$ are dissolved in 20 ml of 90 % strength trifluoracetic acid with ice cooling and the solution is left for 30 minutes at 0°C under nitrogen. Hereafter it is poured into 300 ml of ice-cold peroxide-free ether. The precipitate hereupon produced is suction-filtered, repeatedly washed with peroxide-free ether and dried in vacuo over sodium hydroxide. Hereafter the powder is again dissolved in 20 ml of ice-cold 90 % strength trifluoracetic acid, warmed to 25°C and left for 1 hour at 25°C under nitrogen. The solution is then again poured into 300 ml of ice-cold peroxide-free ether and the resulting precipitate is suction-filtered, washed with ether and dried in vacuo at room temperature over sodium hydroxide. The following operations are carried out under nitrogen and using peroxide-free and oxygen-free solvents.

For conversion to the acetic acid salt the trifluoracetate of I obtained above is dissolved in 20 % strength acetic acid and filtered through a column (1.2 × 15 cm) of a weakly basic ion exchanger resin (Merck No. II, acetate form). The column is rinsed with 20 % strength acetic acid until the U.V.-control of the eluate no longer shows any I to be present. Hereafter the eluate is evaporated in vacuo at 40°C bath temperature with the addition of n-octanol, and the residue is freed of octanol by washing with petroleum ether and is dried. Hereupon the acetic acid salt of the dotriacontapeptide is obtained as a pale yellowish resin. For purification, the product is subjected to a counter-current distribution in the system n-butanol (1 liter)-1 N acetic acid (1 liter)-ammonium acetate (500 mg). For this purpose it is dissolved in 30 ml each of the upper and lower phase of this system and the solution is introduced into the first three tubes of the distribution apparatus. After 250 distribution steps the purity of the individual fractions is tested by means of thin layer chromatography (on an aluminum oxide plate, system 104, Rf=0.50). The pure dotriacontapeptide is in fractions 140 -165 (maximum of the weight curve in fraction 156, K = 1.65). These fractions are combined, evaporated in vacuo at 40°C bath temperature, and the residue is dried at 40°C and 0.01 mm Hg in order to remove ammonium acetate. The dotriacontapeptide hereupon obtained proves to be a single substance according to thin layer chromatography on aluminum oxide (detection by means of Reindel-Hoppe reagent); It shows the following Rf-values:

Rf$_{45}$ = 0.33; Rf$_{52}$ = 0.59; Rf$_{104}$ = 0.56.

The sulphoxide of I shows the following Rf-values: Rf$_{45}$ = 0.30; Rf$_{52}$ = 0.54; Rf$_{104}$ = 0.50.

On electrophoresis on cellulose acetate film ("Cellogel") in acetic acid-formic acid buffer, pH = 1.9, 90 minutes running time, 8 volts/cm, I and its sulphoxide show a running distance of 1.1 cm towards the cathode.

The starting material may be manufactured as follows

1. H-Thr(tBu)-OMe 12.92 g (40mmols) of Z-Thr(tBu)-OMe are hydrogenated in 200 ml of glacial acetic acid and 3 g of Pd-charcoal (10%) at room temperature. The hydrogen uptake is finished after 1 hour. The solution is freed of the catalyst by filtration and is evaporated in a water-pump vacuum at 35°C. After drying in a high vacuum at 35°C 7.3 g of an oil result, which according to a thin layer chromatogram is a single substance and is directly further used.

2. DPC-Ser(tBu)-Thr(tBu)-OMe 19.3 g (38.6 mmols) of DPC-Ser(tBu)-OH, cyclohexylamine salt, are taken up in 500 ml of chloroform and extracted by shaking three times with 25 ml of 1 N citric acid and five times with 40 ml of half-saturated sodium chloride solution at 0°C. The solution is dried over sodium sulphate and then evaporated and the resulting foam is taken up in 250 ml of ethyl acetate. 5.36 ml (38.6 mmols) of triethylamine are added, the solution is cooled to −10°C, and 5.13 ml (38.6 mmols) of isobutyl chlorocarbonate are added whilst stirring. The mixture is stirred for 10 minutes at −10°C and the solution, cooled to −12°C, of 7.3 g (38.6 mmols) of H-Thr(tBu)-OMe in 100 ml of ethyl acetate is then added dropwise in such a way that the reaction temperature never exceeds −10°C. After completion of the addition the mixture is stirred for a further hour at − 10 °C and is then allowed to stand overnight at room temperature. The solution is freed of precipitated triethylamine hydrochloride by filtration and is washed three times with 20 ml of 1 N citric acid at a time and five times with saturated sodium chloride solution at 0°C, dried and evaporated. Crude product (oil): 22.07 g. For purification, 1 g is chromatographed on a silica gel column (2.5 cm, 30 cm). After a first run of 110 ml, 787 mg of pure product are eluted with petroleum ether-ethyl acetate (1:1).

In a thin layer chromatogram on silica gel in toluene-acetone (7:3), Rf = 0.51.

3. Z-Val-Leu-OMe 19.9 g (110 mmols) of H-Leu-OMe. HCl are dissolved in 120 ml of dimethylformamide and 14.6 ml (105 mmols) of triethylamine are added at 0°C. The precipitated triethylamine hydrochloride is filtered off, the filtrate is added to a solution of 25.1 g (100 mmols) of Z-Val-OH in 200 ml of dimethylformamide (0°C), and 22.6 g (110 mmols) of dry dicyclohexylcarbodiimide are then added. After 1 hour's stirring at 0°C and standing overnight in the refrigerator the mixture is filtered and the solution evaporated in a high vacuum at 40°C. The oily residue is taken up in 30 ml of ethyl acetate, and the solution is cooled to 0°C and freed of precipitated dicyclohexylurea. After adding n-hexane the product crystallises out from the filtrate overnight. Melting point 102°–105°C; $[\alpha]_D$: −41° (c = 2.88 in methanol).

In a thin layer chromatogram on silica gel in chloroform-methanol (98:2) Rf = 0.55, and in toluene-acetone (7:3) Rf = 0.60.

4. DPC-Ser(tBu)-Thr(tBu)-NH-NH$_2$ 4.253 g (7.4 mmols) of DPC-Ser(tBu)-Thr(tBu)-OMe in 18 ml of methanol are mixed with 5.55 ml (about 110 mmols) of hydrazine hydrate and allowed to stand for 10 hours at room temperature and 2 hours at 40°C. The reaction solution is taken up in 450 ml of ethyl acetate and is washed four times with half-saturated sodium chloride solution. The solution is dried over sodium sulphate and then concentrated to about 15 ml and mixed with about 5 ml of petroleum ether. Overnight, 3.17 g of the hydrazide of melting point 132°–134°C crystallise out.

In a thin layer chromatogram m silica gel in toluene-acetone (7:3), Rf = 0.40.

5. H-Val-Leu-OMe.HCl 5.66 g (15 mmols) of Z-Val-Leu-OMe are hydrogenated in 75 ml of methanol in the presence of 15 mmols of hydrochloric acid and 850 mg of Pd-charcoal (10%) at room temperature. The hydroen uptake has finished after 3 hours. The catalyst is filtered off and the solution is concentrated to about 15 ml. On addition of ether, the product crystallises out. Melting point 136°–139°C.

In a thin chromatogram on silica gel in chloroform-methanol (9:1) Rf = 0.45; in toluene-acetone (1:1) Rf = 0.43.

6. TRI-Cys(TRI)-Val-Leu-OMe 7.13 g (10 mmols) of TRI-Cys(TRI)-OH.diethylamine salt in chloroform are washed at 0°C with 1 N citric acid and half-saturated sodium chloride solution, the solution is dried and evaporated and the resulting foam is taken up in 50 ml of ethyl acetate. To this is added a solution, at 0°C, of 3.22 g (10 mmols) of H-Val-Leu-OMe,hydrochloride in 40 ml of ethyl acetate to which 1.4 ml (10 mmols) of triethylamine have been added and from which the precipitated triethylamine hydrochloride has been filtered off. 2.26 g (11 mmols) of dry dicyclohexylcarbodiimide are then added at 0°C, and the mixture is stirred for 2½ hours at 0°C and left to stand overnight in the refrigerator. The precipitated dicyclohexylurea is filtered off and the solution is washed at 0°C with 1N citric acid, 1N sodium bicarbonate and half-saturated sodium chloride solution and is dried over sodium sulphate. The solution is concentrated to about 20 ml, cooled to 0°C, and further dicyclohexylurea is filtered off. Evaporation to dryness yields 8.53 g of ester. For purification, the crude product is chromatographed on a silica gel column (5 cm; 55 cm). After a first run of 400 ml the main product is eluted in the pure form by means of 300 ml of petroleum ether-ethyl acetate (1:1).

In a thin layer chromatogram on silica gel in chloroform-methanol (99:1), Rf = 0.43.

7. H-Cys(TRI)-Val-Leu-OMe 11.08 g (13.3 mmols) of TRI-Cys(TRI)-Val-Leu-OMe are dissolved in 75 ml of acetic acid and 12.3 ml of water are added dropwise so that a clear solution always remains. After 1 hour's stirring at room temperature 64 ml of water are added to the clear solution and the precipitate is filtered off and washed with cold 50 % strength acetic acid. The filtrate is evaporated in a high vacuum at 40°C to give an oil, and the latter is taken up in 250 ml of ethyl acetate and is washed at 0°C with 1N sodium bicarbonate and saturated sodium chloride solution. After drying over sodium sulphate the solution is evaporated, whereupon 7.07 g of a white product are obtained. The thin layer chromatogram on silica gel, in the system chloroform-methanol (98:2), shows a spot of Rf-value 0.30 on spraying with Reindel-Hoppe reagent.

8. DPC-Ser(tBu)-Thr(tBu)-Cys(TRI)-Val-Leu-OMe 32.26 ml of hydrochloric acid in ethyl acetate (1.84 N; 59.25 mmols) and 3.26 ml (28.55 mmols) of tert.-butyl nitrite are added at −12°C to 13.6 g (23.8 mmols) of DPC-Ser(tBu)-Thr(tBu)-NH-NH$_2$ in 220 ml of dimethylformamide. After 15 minutes at −10°C a solution, cooled to −10°C, of 14.03 g (23.8 mmols) of H-Cys-(TRI)-Val-Leu-OMe and 8.315 ml (59.25 mmols) of triethylamine in 100 ml of dimethylformamide is added dropwise in such a way that the reaction temperature never exceeds −9°C. The mixture is stirred for a further 1 hour at −10°C and is then allowed to stand overnight at room temperature. The precipitated triethylamine hydrochloride is filtered off, the filtrate is evaporated at 40°C in a high vacuum, and the oily residue is taken up in 500 ml of ethyl acetate, washed with 1N citric acid, 1N sodium bicarbonate and saturated sodium chloride solution, dried, concentrated to about 40 ml and mixed with about 10 ml of petroleum ether. Overnight, the protected pentapeptide ester of melting point 177° – 178°C crystallises out.

In a thin layer chromatogram on silica gel in chloroform-methanol (98:2), Rf = 0.45; in toluene-acetone (7:3), Rf = 0.57.

9. DPC-Ser(tBu)-Thr(tBu)-Cys(TRI)-Val-Leu-OH 2.830 g (2 mmols) of DPC-Ser(tBu)-Thr(tBu)-Cys(-TRI)-Val-Leu-OMe are dissolved in 60 ml of 75 % strength dioxane and 3 ml of 2N sodium hydroxide solution (6 mmols) are added. After 1½ hours at room temperature the dioxane is evaporated off at 40°C in a waterpump vacuum, ethyl acetate and water are added and the pH is adjusted to 3 at 0°C by means of 1N citric acid. The ethyl acetate phase is washed with sodium chloride solution, dried and evaporated. A product results which according to a thin layer chromatogram on silica gel is a single substance. Rf in chloroform-methanol (7:3) = 0.40; $Rf_{45}$ = 0.55.

10. H-Ser(tBu)-Thr(tBu)-Cys(TRI)-Val-Leu-OH 2.22 g (2 mmols) of DPC-Ser(tBu)-Thr(tBu)-Cys(TRI)-Val-Leu-OH are dissolved in 20ml of methylene chloride and 12 ml of chloracetic acid in water (made up of 75 g of chloracetic acid and 25 ml of water) are added. The clear solution is stirred for 15 minutes at room temperature, cooled to 0°C, and 70 ml of water are then added. The pH is adjusted to 6.5 with concentrated ammonia, whereupon the product precipitates. The aqueous solution is decanted and the residue is further triturated three times with water and then lyophilised. Triturating the product three times with ether yields a white powder which according to a thin layer chromatogram is a single substance. It is further used in this form.

In a thin layer chromatogram on silica gel, $Rf_{45}$ = 0.48; $Rf_{101}$ = 0.65; $Rf_{52}$ = 0.75.

11. Z-Asn-Leu-OMe 16.7 g of H-Leu-OMe and 46.0 g of Z-Asn-ONP are dissolved in 100 ml of freshly distilled dimethylformamide. The solution is allowed to stand for 19 hours at 25°C. Thereafter 1.2 liters of water are added and the crystalline precipitate is filtered off. The dipeptide derivative is dried at 40°C in vacuo and is then twice recrystallised from methanol-water. Melting point 180° – 181°C; $[\alpha]_D^{20}$ = +9° (c = 2.05 in chloroform).

12. H-Asn-Leu-OMe 15.0 g of Z-Asn-Leu-OMe are dissolved in 400 ml of t-butanol-water (9:1) and are hydrogenated in the presence of 2 g of palladium-charcoal (10 %Pd). After completion of the hydrogenation the catalyst is filtered off and the solution evaporated at 40°C. The residue is directly further used.

13. Z-Ser(tBu)-Asn-Leu-OMe 8.90 g of H-Asn-Leu-OMe and 11.0 g of Z-Ser(tBu)-OH are dissolved in 100 ml of freshly distilled dimethylformamide. The solution is cooled to 0°C and 3.90 g of N-hydroxysuccinimide followed by 8.70 g of dicyclohexylcarbodiimide are added. After 30 minutes standing at 0°C and 18 hours at 25°C the precipitated dicyclohexylurea is filtered off and the filtrate is poured into 800 ml of ice water. The crystalline precipitate which hereupon separates out is dried in vacuo at 40°C and then recrystallised from methanol-water. The Z-Ser(tBu)-Asn-Leu-OMe which is hereupon obtained in an analytically pure form melts at melting point 202° – 205°C; $[\alpha]_D^{20}$ = –18° (c = 1.05 in glacial acetic acid).

14. H-Ser(tBu)-Asn-Leu-OMe 6.3 g of Z-Ser(tBu)-Asn-Leu-OMe are dissolved in 600 ml of methanol and hydrogenated in the presence of 1.2 g of palladium-charcoal (10 % Pd). After 1.25 hours the catalyst is filtered off and the solution evaporated to dryness in vacuo at 30°C bath temperature. The crystalline tripeptide derivative thereupon obtained shows Rf = 0.11 on thin layer chromatography on silica gel plates in the system chloroform-methanol (90:10).

15. BOC-Cys(TRI)-Ser(tBu)-Asn-Leu-OMe 5.0 g of H-Ser(tBu)-Asn-Leu-OMe and 6.7 g of BOC-Cys(TRI)-ONP are dissolved in 30 ml of freshly distilled dimethylformamide. The yellow solution is allowed to stand for 42 hours at 26°C. Thereupon the mixture is precipitated by adding 500 ml of ice water and the precipitated product is filtered off. It is dissolved in ethyl acetate and the solution is washed with 5 % strength citric acid solution and then with water. Thereupon it is washed, whilst cooling with ice, five times with a mixture of, in each case, 1 part by volume of 5 % strength potassium carbonate solution and 5 % strength potassium bicarbonate solution in order to remove p-nitrophenol, and then with water. The ethyl acetate solution on drying and evaporation leaves a resin-like product. This is reprecipitated four times from acetone and petroleum ether. The tetrapeptide derivative thereupon obtained as a solid powder shows a melting point of 181°– 182°C; $[\alpha]_D^{20}$ = –11° (c = 2.09 in methanol).

On thin layer chromatography on silica gel plates $Rf_{43A}$ = 0.57; Rf in ethyl acetate = 0.10; Rf in toluene-acetone (7:3) = 0.05; Rf in chloroform-methanol (9:1) = 0.45.

16. BOC-Cys(TRI)-Ser(tBu)-Asn-Leu-NH-NH$_2$ 7.0 g of BOC-Cys(TRI)-Ser(tBu)-Asn-Leu-OMe are dissolved in 70 ml of methanol and the solution cooled to 0°C is mixed with 7 ml of hydrazine hydrate. After 16 hours at 2°C an ice-cold solution of 600 ml of 2N acetic acid is added, and the jelly-like precipitate is thoroughly triturated, filtered and washed with a large amount of water until neutral. The resulting powder is dried at 40°C in vacuo and is then suspended in 100 ml of acetonitrile. After trituration, the product is filtered off and dried at 40°C in vacuo. The resulting BOC-Cys(TRI)-Ser(tBu)-Asn-Leu hydrazide shows a melting point of 216°– 218°C.

On thin layer chromatography on silica gel plates it shows the following Rf-values; Rf = 0.55 in dioxane-water (98.2); Rf = 0.52 in chloroform-methanol (8:2); $Rf_{102E}$ = 0.70.

17. BOC-Cys(TRI)-Ser(tBu)-Asn-Leu-Ser(tBu)-Thr(tBu)-Cys(TRI)-Val-Leu-OH 1.71 ml of hydrochloric acid in ethyl acetate (1.84 N; 3.15 mmols) and 0.174 ml (1.51 mmols) of tert.-butyl nitrite (1.74 ml of a solution of 1 ml of tert.-butyl nitrite made up to 10 ml with dimethylformamide) are added at –15°C to 1.075 g (1.26 mmols) of BOC-Cys(TRI)-Ser(tBu)-Asn-Leu-NH-NH$_2$ in 15 ml of dimethylformamide. The solution is stirred for 15 minutes at –10°C and then the solution of 1.104 g (1.26 mmols) of H-Ser(tBu)-Thr-(tBu)-Cys(TRI)-Val-Leu-OH and 0.61 ml (4.41 mmols) of triethylamine in 15 ml of dimethylformamide, cooled to –12°C, is added dropwise. The reaction mixture is stirred for 1 hour at –10°C and 4 hours at room temperature. After evaporation to a small volume in a high vacuum and addition of water, a powdery product is obtained which is twice triturated with water and then dried in a high vacuum over potassium hydroxide. This crude product is purified by recrystallisation from methanol. A white powder separates out overnight at 0°C from a methanolic solution which has been saturated at 50°C, and this powder proves to be a single substance in a thin layer chromatogram.

In a thin layer chromatogram on silica gel $Rf_{43C}$ = 0.54; $Rf_{121A}$ = 0.65; $Rf_{45}$ = 0.50; $Rf_{70}$ = 0.75; Rf in chloroform-methanol (8:2) = 0.40.

18. BOC-C̲ys-Ser(tBu)-Asn-Leu-Ser(tBu)-Thr(tBu)-C̲ys-Val-Leu-OH a. 846 mg (0.5 mmols) of BOC-Cys(TRI)-Ser(tBu)-Asn-Leu-Ser(tBu)-Thr-(tBu)-Val-Leu-OH are dissolved in 8 ml of dimethylformamide and 350 mg (1.1 mmols) of mercury (II) acetate in 4 ml of methanol are added. After about 5 minutes a jelly-like product begins to separate out from the clear solution. The reaction mixture is stirred for 60 minutes at room temperature, diluted with 50 ml of dimethylformamide, and then hydrogen sulphide is passed through for 20 minutes and nitrogen for 15 minutes. The black precipitate is filtered off through "Celite" and is washed with dimethylformamide. The filtrate is concentrated to 40 ml and nitrogen passed through it for 15 minutes. This solution is added dropwise, simultaneously with a solution of 170 mg (0.6 mmols) of diiodoethane in 40 ml of methanol, to 20 ml of dimethylformamide and 20 ml of methanol at room temperature over the course of 1 hour, whilst stirring. After 10 hours at room temperature the solvent is evaporated off in a high vacuum at 40°C and the oily residue is first triturated three times with petroleum ether, then twice with water, and is lyophilised. The purification of the brownish crude product is achieved by counter-current distribution in the system: methanol-buffer-chloroform-carbon tetrachloride (10:3:5:4). The buffer is obtained from 28.6 ml of glacial acetic acid and 19.25 g of ammonium acetate, made up to 1 liter with water. After 135 distribution stages the product is present in elements 49 - 63 ($r_{max} = 53$; $K = 0.65$). The content of these elements is evaporated to dryness and is freed of ammonium acetate overnight in a high vacuum at 40°C. 254 mg of a product which is chromatographically a single substance are obtained.

In a thin layer chromatogram on silica gel $Rf_{45} = 0.42$; $Rf_{121A} = 0.70$; $Rf_{70} = 0.75$; $Rf_{53} = 0.43$; $Rf_{43A} = 0.22$ b. 2.50 Grams (14.78 mmols) of BOC-Cys(TRI)-Ser(tBu)-Asn-Leu-Ser(tBu)-Thr(tBu)-Cys(TRI)-Val-Leu-OH in 500 ml of methanol are dropped within 45 minutes into a stirred solution of 3.73 g (14.78 mmols) of iodine in 500 ml of methanol at room temperature. When all has been entered the batch is stirred on for 1 hour and the solution is then decolorized at 0°C with aqueous thiosulphate solution (26.05 ml N-thiosulphate). The clear solution is concentrated to about 100 ml at 30°C under a water-jet vacuum. Then 1.5 liters of water are added, the precipitated product is filtered off and washed with water and dried over potassium hydroxide. Yield: 2.32 g of crude product; it is twice triturated with petroleum ether and purified by a counter-current distribution in the system methanol + buffer + chloroform + carbon tetrachloride (10:3:5:4). [Buffer: 28.6 ml of glacial acetic acid, 19.25 g of ammonium acetate, made up to 1 liter with water]. After 135 steps the main product is found in the elements 50 - 79 ($r_{max} = 64$; $K = 0.96$). The content of these elements is combined and evaporated to dryness at 40°C under a high vacuum, the ammonium acetate is expelled by sublimation. The resulting BOC-Cys-Ser(tBu)-Asn-Leu-Ser(tBu)-Thr-(tBu)-Cys-Val-Leu-OH (1.49 g = 83% of theory) is revealed by its thin-layer chromatogram on silica gel to be unitary. It exhibits the same Rf values as the product described under (a).

19. Z-Tyr(tBu)-Try-OMe 11.1 ml of triethylamine and 20.5 g of H-Try-OMe hydrochloride are added to a solution of 29.8 g of Z-Tyr(tBu)-OH in 190 ml of chloroform, and the mixture is stirred for 30 minutes at room temperature and then cooled to 0°C. A solution of 29.9 g of dicyclohexylcarbodiimide in 50 ml of chloroform is added dropwise at this temperature. The mixture is stirred for 1 hour at 0°C and overnight at room temperature. After filtering off the dicyclohexylurea the solution is concentrated in vacuo, the residue is taken up in ethyl acetate, and this solution is extracted by shaking at 0°C with 5% strength citric acid solution and 2N sodium carbonate. The oil obtained after evaporation of the ethyl acetate is chromatographed on 1 kg of silica gel. The crude product, in 250 ml of toluene, is applied to the column and eluted with 9 liters of toluene, 6.5 litres of toluene-chloroform (9:1) and 15 liters of toluene-chloroform (1:1). The fractions, which according to a thin layer chromatogram are pure, are combined and evaporated to dryness in vacuo. 27.9 g of Z-Try(tBu)-Try-OMe are obtained; Rf = 0.65 in chloroform-acetone (1:1), on silica gel.

20. H-Tyr(tBu)-Try-OMe 26.2 g of Z-Tyr(tBu)-Try-OMe are dissolved in 520 ml of methanol and hydrogenated at room temperature in the presence of 4 g of 10% strength palladium-charcoal and 21.8 ml of 2.1N hydrochloric acid. After completion of the hydrogenation the catalyst is filtered off and the filtrate is evaporated to dryness in vacuo at 30°C. 22.0 g of H-Tyr(tBu)-Try-OMe hydrochloride, Rf = 0.45 in chloroform-acetone (1:1), are obtained.

21. Z-Ala-Tyr(tBu)-Try-OMe 20.8 g of H-Tyr(tBu)-Try-OMe. HCl are dissolved in 40 ml of dimethylformamide, 16.7 g of Z-Ala-ONP and 6.1 ml of triethylamine are added and the mixture is stirred until it crystallises throughout. After standing overnight, 300 ml of ethyl acetate are added, the insoluble material is filtered off and the filtrate is washed at 0°C with dilute potassium carbonate solution until free of nitrophenol and is then extracted by shaking with 0.1 M citric acid and water. After drying the solution and evaporating the ethyl acetate the residue is dissolved in 25 ml of chloroform, adsorbed on a column of 200 g of silica gel, and eluted with chloroform. The resulting product is recrystallised from ethyl acetate-hexane. The Z-Ala-Tyr(tBu)-Try-OMe melts from 108° onwards, with slow decomposition, Rf = 0.5 in chloroform-acetone (1:1).

22. H-Ala-Tyr(tBu)-Try-OMe 10.3 g of carbobenzoxy compound of 21 are hydrogenated in 200 ml of methanol in the presence of 0.5 g of 10% strength palladium-charcoal, as previously indicated. The decarbobenzoxylated product shows Rf = 0.3 in the system chloroform-methanol (9:1).

23. DPC-Ser(tBu)-Ala-Tyr(tBu)-Try-OMe 8.3 g of DPC-Ser(tBu)-OH (liberated from the cyclohexylammonium salt by means of citric acid) in 25 ml of ethyl acetate are mixed at −10°C with 2.7 ml of triethylamine and 2.7 ml of chloroformic acid isobutyl ester. After 5 minutes at −10°C the solution of 8.1 g of H-Ala-Tyr(tBu)-Try-OMe in 20 ml of dimethylformamide is added to the mixed anhydride and the mixture is stirred for 10 minutes at −10°C, 2 hours at 0°C and 12 hours at room temperature. The mixture is diluted with ethyl acetate, extracted by shaking at 0°C with 0.1 M citric acid and saturated potassium carbonate solution and is then washed at room temperature with water, dried and evaporated to dryness in vacuo. The residue is recrystallised from ethyl acetate-hexane. 10.5 g of DPC-Ser(tBu)-Ala-Tyr(tBu)-Try-OMe of melting point 148°– 149°C (decomposition) are obtained. Rf = 0.7 in the system chloroform-methanol (9:1).

24. DPC-Ser(tBu)-Ala-Tyr(tBu)-Try-NH-NH$_2$ 1.34 g of the tetrapeptide derivative of 23 are dissolved in 7.5 ml of methanol, 0.75 ml of hydrazine hydrate are added and the mixture is allowed to stand for 24 hours at room temperature. On adding 7.5 ml of methanol and 15 ml of water the DPC-Ser(tBu)-Ala-Tyr(tBu)-Try-NH-NH$_2$ crystallises out. The product is filtered off, thoroughly washed with 50 % strength methanol and water, and dried in a high vacuum over concentrated sulphuric acid. The product melts from 136°C onwards, with slow decomposition. Rf = 0.35 in the system chloroform-methanol (9:1).

25. Z-Asn-Phe-NHNH-BOC 1.4 g of H-Phe-NHNH-BOC, 1.94 g of Z-Asn-ONP and 3 ml of dimethylformamide are stirred at room temperature until the mixture solidifies. After allowing to stand overnight, the material is triturated with ether, and the dipeptide derivative is filtered off and washed with ether until free of nitrophenol. The product begins to melt at 211°C with decomposition. Rf = 0.55 in chloroform-methanol (8:2) on silica gel.

26. H-Asn-Phe-NH-NH-BOC

28.75 g of the carbobenzoxy compound of 25, dissolved in 1 liter of methanol, are hydrogenated at room temperature in the presence of 2.9 g of 10 % strength palladium-charcoal. After complete decarbobenzoxylation the catalyst is filtered off and the filtrate is evaporated to dryness. The product melts at 160°–161°C. Rf = 0.15 in chloroform-methanol (8:2).

27. Z-Asn-Asn-Phe-NH-NH-BOC 20.93 g of H-Asn-Phe-NH-NH-BOC are dissolved in 45 ml of dimethylformamide with warming, mixed with 22.7 g of Z-Asn-ONP at room temperature, and stirred until the mixture solidifies. After standing overnight, the solid mass is dissolved in 160 ml of dimethylformamide with warming, precipitated by adding dropwise to 1 liter of ether, and the product is filtered off and washed with acetone until free of nitrophenol. Rf = 0.24 in chloroform-methanol (8:2).

28. H-Asn-Asn-Phe-NHNH-BOC

35.8 g of the carbobenzoxy compound described under 27 are dissolved in 560 ml of dimethylformamide with warming. After cooling to room temperature 3.6 g of 10 % palladium-charcoal are added and the material is hydrogenated. After complete decarboxyloxylation the catalyst is filtered off, the dimethylformamide solution is concentrated to about 100 ml, and the H-Asn-Asn-Phe-NHNH-BOC is precipitated by adding dropwise to 1 liter of ether. Rf$_{100}$ = 0.35 on silica gel.

29. Z-Leu-Asn-Asn-Phe-NHNH-BOC 26.5 g of H-Asn-Asn-Phe-NHNH-BOC are dissolved in 58 ml of warm dimethylformamide, a solution of 24.2 g of Z-Leu-ONP in 16 ml of dimethylformamide is added at room temperature, and the mixture is stirred until it solidifies. After standing overnight the mixture is triturated with ether, filtered off, dissolved in 190 ml of dimethylformamide, and the product reprecipitated by adding dropwise to 1.5 liters of ether. The product is filtered off and washed with ether until free of nitrophenol. Rf = 0.45 in the system chloroform-methanol (7:3) on silica gel.

30. H-Leu-Asn-Asn-Phe-NHNH-BOC 36.0 g of the carbobenzoxy derivative obtained under 29 are hydrogenated in 800 ml of dimethylformamide as described under 28 and are worked-up. 27.9 g of H-Leu-Asn-Asn-Phe-NHNH-BOC are obtained. Rf$_{100}$ = 0.35.

31. Z-Asn-Leu-Asn-Asn-Phe-NH-NH-BOC 27.9 g of H-Leu-Asn-Asn-Phe-NH-NH-BOC are dissolved in 145 ml of warm dimethylformamide, mixed at room temperature with a solution of 21.6 g of Z-Asn-ONP in 20 ml of dimethyformamide and stirred until the mixture solidifies. After allowing to stand overnight the mixture is worked-up as described under 29. 34.2 g = 88 % of theory, of the pentapeptide derivative are obtained. Rf$_{100}$ = 0.5.

32. H-Asn-Leu-Asn-Asn-Phe-NH-NH-BOC 34.2 g of the pentapeptide derivative described under 31 are hydrogenated as described under 30 and worked-up. The H-Asn-Leu-Asn-Asn-Phe-NH-NH-BOC shows Rf$_{100}$ = 0.2.

33. Z-Arg-Asn-Leu-Asn-Asn-Phe-NH-NH-BOC hydrochloride

23.6 g of Z-Arg-OH are suspended in 87 ml of dimethylformamide and mixed with 21.2 ml of 3.6 N hydrochloric acid in dioxane whilst cooling with cold water, whereupon solution takes place. 28.2 g of the pentapeptide derivative mentioned under 32) are dissolved in 440 ml of warm dimethylformamide, cooled to room temperature, and added to the solution of Z-Arg-OH.HCl, followed by 17.4 g of dicyclohexylcarbodiimide. The mixture is stirred for 24 hours, the dicyclohexylurea which has crystallised out is filtered off, and the filtrate is concentrated to about 250 ml. The crude product is precipitated by adding this solution dropwise to 2 liters of ether. The product is dissolved by introducing it into 280 ml of hot dimethylformamide with stirring. After cooling to room temperature the product is precipitated with 870 ml of saturated sodium chloride solution and 1740 ml of water. The precipitated product is filtered off and thoroughly washed with half-saturated sodium chloride solution. The moist filter residue is dissolved in 1 liter of warm dimethylformamide and azeotropically dehydrated by twice concentrating the solution. The precipitated sodium chloride is filtered off, the filtrate is added dropwise to 2.4 liters of acetonitrile, and the resulting precipitate is filtered off after a few hours, washed with acetonitrile and ether, and dried in vacuo at 40°C. The Z-Arg-Asn-Leu-Asn-Asn-Phe-NH-NH-BOC hydrochloride shows Rf$_{100}$ = 0.25.

34. Z-Arg-Asn-Leu-Asn-Asn-Phe-NHNH$_2$ hydrochloride 10.6 g of the hexapeptide derivative described under 33 are dissolved in 50 ml of 90 % strength trifluoracetic acid whilst stirring and cooling in ice, and the solution warmed to room temperature and left for 20 minutes at this temperature. Thereafter the solution is added dropwise to 500 ml of ether whilst stirring and cooling with ice, and the precipitate is filtered off and washed with ether until free of acid. The product is introduced into 90 ml of warm dimethylformamide, stirred for some time, and then precipitated in a powdery form by means of 1 liter of ether. This crude product is stirred for 1 hour with 170 ml of isopropanol at room temperature, filtered off, washed with isopropanol and ether and dried in vacuo at 40°C. The Z-Arg-Asn-Leu-Asn-Asn-Phe-NHNH$_2$ hydrochloride, showing Rf$_{96}$ = 0.38 on silica gel, is obtained.

35. Z-Phe-Ser(tBu)-OCH$_3$ 27.0 g (90 mmols) of Z-Phe-OH are dissolved in 250 ml of absolute tetrahydrofurane together with 12.5 ml (90 mmols) of triethylamine, and cooled. 14.7 ml (112 mmols) of chlorocarbonic acid isobutyl ester are added dropwise at −18°C and the mixture is stirred for one-half an hour at ≤−10°C. 18.1 g of H-Ser(tBu)-OCH$_3$ hydrochloride (85.5 mmols) in a finely powdered form are now added to the white suspension (triethylamine hydrochloride), the mixture is diluted with 350 ml of tetrahydrofurane, and 15.0 m (108 mmols) of triethylamine in 100 ml of tetrahydrofurane are then added dropwise. The mixture is stirred for a further 3 hours at about −10°C and then overnight at room temperature. The suspension is then concentrated to about 250 ml in vacuo, taken up in a large amount of ethyl acetate and extracted by shaking with dilute citric acid solution (3 × 200 ml), dilute sodium carbonate solution (3 × 200 ml) and saturated sodium chloride solution (5 × 200 ml), dried over sodium sulphate and evaporated. The crude product is dissolved in 200 ml of ethyl acetate-hexane (1 : 1). White husks crystallise out of the solution on cooling and these are isolated and dried. The product melts at 92.5°– 94°C. $[\alpha]_D^{20} = 3° ± 0.5°$ (c = 2.2 % in methanol).

On thin layer chromatography on silica gel plates the product shows the following Rf-values: in chloroform-acetone (1:1) Rf = 0.70; in chloroform-methanol (95:5) Rf = 0.70; $Rf_{43A} = 0.65$; $Rf_{89} = 0.86$.

36. Z-Phe-Ser(tBu) hydrazide 25.4 g of Z-Phe-Ser(tBu)-OCH$_3$ (55.7 mmols) are dissolved in 250 ml of methanol and 28 ml (575 mmols) of hydrazine hydrate are added whilst cooling with ice. The solution is left for 67 hours in the refrigerator, whereupon a thick crystal cake forms. The product is isolated and dried. It melts at 158.5°– 159.5°C. $[\alpha]_D^{20} = +16° ± 0.5°$ (c = 2.3% in glacial acetic acid). In a thin layer chromatogram on silica gel layers Rf = 0.27 in chloroform-methanol (95:5); $Rf_{43A} = 0.57$; $Rf_{89} = 0.65$.

37. Z-Phe-Ser(tBu)-Gly-OCH$_3$ 18.4 g of Z-Phe-Ser(tBu) hydrazide (40.4 mmols) are dissolved in 100 ml of dimethylformamide and 41.6 ml of hydrogen chloride in ether (2.43 N, 101 mmols) are added at −20°C. 7.15 ml of t-butyl nitrite (59 mmols) in 40 ml of dimethylformamide are added to the clear solution and rinsing is effected with 20 ml of dimethylformamide. After 10 minutes at temperatures below −9°C 14.0 ml (101 mmols) of triethylamine in 60 ml of dimethylformamide are added and 8.85 g of H-Gly-OCH$_3$ hydrochloride (70 mmols) are introduced. Three portions each of 5.6 ml of triethylamine are added at intervals of 10 minutes (a total of 121 mmols). The pH is then about 8.5. The cooling mixture is then removed and the reaction mixture stirred for 3 hours at 0°C and then overnight at room temperature. After concentrating the reaction mixture in vacuo to give a thick paste, the latter is taken up in a large amount of ethyl acetate and the solution is successively washed with three portions of dilute citric acid solution, three portions of dilute sodium carbonate solution and five portions of saturated sodium chloride solution. The crude product obtained after drying and evaporating the solution is dissolved in ethyl acetate, filtered through a glass frit and mixed with about 800 ml of ether. The protected tripeptide ester crystallises out very slowly, melting point 140°– 141°C. $[\alpha]_D^{20} = +13° ± 0.5°$ (c = 2.3% in glacial acetic acid).

In a thin layer chromatogram on silica gel layers Rf = 0.61 in chloroform-methanol (95:5); in chloroform-acetone (9:1), Rf = 0.28; $Rf_{102E} = 0.82$; $Rf_{43C} = 0.72$.

38. H-Phe-Ser(tBu)-Gly-OCH$_3$ 7.4 g of Z-Phe-Ser(tBu)-Gly-OCH$_3$ are decarbobenzoxylated in methanol with hydrogen in the presence of 1.0 g of palladium charcoal (10% Pd). After completion of the water uptake the solution is filtered, evaporated, and the resulting crude product directly further processed. The product shows the following Rf-values in a thin layer chromatogram on silica gel layers: in chloroform-methanol (95:5): Rf = 0.26; $Rf_{43A} = 0.60$; $Rf_{52} = 0.51$.

39. Z-Arg-Phe-Ser(tBu)-Gly-OCH$_3$ hydrobromide 5.3 g of Z-Arg-OH (17.3 mmols) are suspended in 15 ml of dimethylformamide and after cooling with an ice-sodium chloride mixture, 5.9 ml of hydrobromic acid in methanol (3.06 N, 18 mmols) are added. After brief stirring a clear colourless solution is produced. A solution of 5.6 g of H-Phe-Ser(tBu)-Gly-OCH$_3$ (14.4 mmols) in 15 ml of dimethylformamide is added dropwise thereto at −18°C and a further 7 ml of dimethylformamide are added. A solution of 3.85 g of dicyclohexylcarbodiimide in 5 ml of methylene chloride is then added, the cooling mixture is replaced by ice water after 1 hour, and after a further 3 hours the reaction mixture is stirred overnight at room temperature. The precipitate of dicyclohexylurea which has separated out is then filtered off and the filtrate is concentrated in vacuo to half its volume, cooled to 0°C and stirred into 600 ml of ether. The solution is decanted from the resulting precipitate, and the precipitate is washed with ether, dissolved in about 50 ml of methanol and again precipitated with 600 ml of ether. After again dissolving in methanol, the material is evaporated and dried in a high vacuum. In a thin layer chromatogram on silica gel layers the product shows: $Rf_{52} = 0.48$; $Rf_{100} = 0.54$; on Selekta cellulose $Rf_{45} = 0.81$.

40. H-Arg-Phe-Ser(tBu)-Gly-OCH$_3$ hydrochloride-hydrobromide 6.3 g of Z-Arg-Phe-Ser(tBu)-Gly-OCH$_3$ hydrobromide (8.5 mmols) are dissolved in 350 ml of methanol and 2.9 ml of hydrogen chloride in dioxane (3.09 N, 8.9 mmols) are added. The mixture is hydrogenated in the presence of 1.2 g of 10% strength palladium-charcoal at room temperature and atmospheric pressure. After completion of the hydrogen uptake the solution is filtered and evaporated and the resulting residue is dissolved in 30 ml of methanol and the solution stirred into 700 ml of ether. Thereby a yellowish paste is produced which is again dissolved and precipitated in the same manner.

Finally, the product is again dissolved in methanol, filtered and evaporated. The product shows the following values in a thin layer chromatogram on silica gel layers: $Rf_{59} = 0.12$; $Rf_{96} = 0.38$; $Rf_{100} = 0.13$.

41. Z-His-Arg-Phe-Ser(tBu)-Gly-OCH$_3$ 7.6 g of Z-His-NH-NH$_2$ (25 mmols) are suspended in 60 ml of dimethylformamide, 31 ml of hydrogen chloride in ether (2.43 N, 75.3 mmols) are added at −16°C and the clear yellowish solution thereby obtained is mixed, at −18°C, with 3.2 ml of t-butyl nitrite (95% strength, 26.5 mmols) in 10 ml of dimethylformamide. After 10 minutes 10.4 ml of triethylamine (75 mmols) in 25 ml of pre-cooled dimethylformamide, and 8.5 g of H-Arg-Phe-Ser(tBu)-Gly-OCH$_3$. 2 HCl (14 mmols) in 50 ml of pre-cooled dimethylformamide are added. The mixture is diluted with 40 ml of dimethylformamide and four portions each of 1.0 ml of triethylamine (a total of 28.7 mmols) are added in intervals of 5 minutes. The mixture is allowed to stand for a further 3 hours at 0°C and for 20 hours at room temperature, the precipitated salts are then filtered off, and the reaction solution is concentrated in vacuo to about three-fourths of its volume. On repeatedly stirring the product into a large amount of ethyl acetate a crude product is obtained which is purified by counter-current distribution in the system methanol-buffer-chloroform-carbon tetrachloride (9:3.5:8:2) through 130 stages (buffer as under 18); $r_{max} = 54$; $K = 0.7$. The pure fractions are combined, evaporated, freed of ammonium acetate in a high vacuum at 40°C, and lyophilised after solution in water.

In a thin layer chromatogram on silica gel layers $Rf_{52A} = 0.34$; $Rf_{101A} = 0.71$; $Rf_{121} = 0.76$; $Rf_{111A} = 0.40$.

42. H-His-Arg-Phe-Ser(tBu)-Gly-OCH$_3$. 2 CH$_3$-COOH 2.9 g of Z-His-Arg-Phe-Ser(tBu)-Gly-OCH$_3$ (3.3 mmols) are hydrogenated in 300 ml of methanol-glacial acetic acid (9:1), with the addition of 500 mg of palladium-charcoal (10% Pd), at room temperature and atmospheric pressure. After completion of the hydrogen uptake the solution is filtered and evaporated to dryness in vacuo, with twice 50 ml of toluene at a time being evaporated over the residue. The product, a white powder, shows the following Rf-values in thin layer chromatograms on silica gel plates: $Rf_{101B} = 0.51$; $Rf_{96} = 0.10$; $Rf_{111A} = 0.28$; on Selekta cellulose $Rf_{45} = 0.55$; $Rf_{52A} = 0.44$.

43. H-His-Arg-Phe-Ser(tBu)-Gly-OH.CH$_3$-COOH 2.84 g of H-His-Arg-Phe-Ser(tBu)-Gly-OCH$_3$. 2CH$_3$-COOH are dissolved in 40 ml of water and stirred for 14 minutes at room temperature with 15 ml of 2 N piperidine solution in water. The clear slightly yellow solution is then neutralised with 15 ml of 2 N aqueous acetic acid, filtered and lyophilised. Piperidine acetate is driven off from the lyophilised product, a slightly yellow deliquescent mass, in a high vacuum on a water bath at 60°C. The residue is now dissolved in 10 ml of methanol and stirred into 400 ml of ethyl acetate. The white flocculent precipitate is filtered, washed with ethyl acetate and dried. 2.0 g of pure product are obtained in the form of a white powder.

In a thin layer chromatogram on silica gel layers $Rf_{101B} = 0.45$; $Rf_{121} = 0.47$; on Selekta cellulose: $Rf_{45} = 0.48$; $Rf_{55} = 0.38$; $Rf_{96} = 0.36$.

In paper electrophoresis (paper S + S 2043 6; 5 hours; 2000 volts; pH 6.3) the substance migrates 6.5 cm towards the cathode. In electrophoresis on Selekta cellulose plates (pH 6.3; 3 hours; 1000 volts) the substance migrates 8.5 cm towards the cathode.

44. Z-Arg-Asn-Leu-Asn-Asn-Phe-His-Arg-Phe-Ser(tBu)-Gly-OH. CH$_3$-COOH C 3.77 g of Z-Arg-Asn-Leu-Asn-Asn-Phe-NH-NH$_2$ are suspended in 100 ml of dimethylformamide and after cooling by means of an ice-sodium chloride bath 3.0 ml of hydrogen chloride in dioxane (3.09 N, 9.27 mmols) are added. A part of the suspension dissolves. 0.5 ml of t-butyl nitrite (95% strength, 4.14 mmols) are now added at −10°C. After 5 minutes at −10° to −12°C 0.08 ml of t-butyl nitrite are again added. After a total of 11 minutes reaction time 1.29 ml of triethylamine (9.26 mmols) are added followed immediately by the precooled solution of 2.40 g of H-His-Arg-Phe-Ser(tBu)-Gly-OH.CH$_3$-COOH (3.6 mmols) in 30 ml of dimethylformamide, and a further 20 ml of cold dimethylformamide are then added. 1.08 ml of triethylamine (7.8 mmols) are now added in four portions over the course of 2.5 hours; the pH varies between 7 and 8. The mixture is left overnight at 0°C and in the morning a solution of the azide prepared from 1.81 g of Z-Arg-Asn-Leu-Asn-Asn-Phe-NH-NH$_2$ in the same manner as described above is added, followed by a further 0.62 ml (4.47 mmols) of triethylamine. The mixture is again left overnight at 0°C, concentrated to a volume of about 15 ml in vacuo at a bath temperature of 45°C in the morning, and stirred into 800 ml of ethyl acetate. The crude product is filtered off and washed with ethyl acetate and dried. It is subjected to a counter-current distribution in the system n-butanol-glacial acetic acid-water (4:1:5) over 300 stages; $r_{max} = 94$; $K = 0.46$. The pure fractions detected by thin layer chromatography are combined, evaporated, dissolved in water, filtered and lyophilised. In a thin layer chromatogram on silica gel layers the product shows: $Rf_{101b} = 0.56$; $Rf_{104} = 0.07$; on Selekta cellulose: $Rf_{45} = 0.37$.

45. H-Arg-Asn-Leu-Asn-Asn-Phe-His-Arg-Phe-Ser(tBu)-Gly-OH. 2 CH$_3$-COOH 1.48 g of Z-Arg-Asn-Leu-Asn-Asn-Phe-His-Arg-Phe-Ser(tBu)-Gly-OH are hydrogenated in 350 ml of dimethylformamide-water (4:1) with addition of 700 mg of 10% strength palladium-charcoal, at room temperature and atmospheric pressure. After 15 hours shaking under a hydrogen atmosphere the solution is filtered, evaporated in vacuo, dissolved in water and lyophilised. The pure product shows the following Rf-values in a thin layer chromatogram on silica gel plates: $Rf_{101B} = 0.42$; $Rf_{101A} = 0.34$; on Selekta cellulose: $Rf_{45} = 0.27$; on Alox-Camag: $Rf_{52A} = 0.51$; $Rf_{111A} = 0.28$; $Rf_{121} = 0.27$.

46. DPC-Ser(tBu)Ala-Tyr(tBu)-Try-Arg-Asn-Leu-Asn-Asn-Phe-His-Arg-Phe-Ser(tBu)-Gly-OH 765 mg of DPC-Ser(tBu)-Ala-Tyr(tBu)-Try-NHNH$_2$ in 15 ml of degassed dimethylformamide are mixed at −30°C with 0.6 ml of 3.6 N hydrogen chloride in dioxane and subsequently with 0.124 ml of t-butyl nitrite. After 15 minutes at −15°C 1.7 ml of 2 N sodium carbonate solution are added dropwise (pH 7 – 8) and the azide is precipitated by means of ice-cold water. The precipitate is filtered off and washed with ice-cold water. 272 mg of H-Arg-Asn-Leu-Asn-Asn-Phe-His-Arg-Phe-Ser(tBu)-Gly-OH.acetate are dissolved in 5.5 ml of dimethylformamide by gentle warming, 0.51 ml of 1 M triethylamine in dimethylformamide are added at room temperature and the solid azide manufactured above is mixed with the solution at 0°C. The filter is further rinsed with 4 ml of cold dimethylformamide and 2 ml of cold ethyl acetate. The solution is not stirred at 0°C, with 0.5 ml of water being added after 20 minutes and 0.05 ml of 1 M triethylamine in dimethylformamide being added after 2 hours. After 4 hours the reaction mixture is precipitated with a large amount of ether. Hereupon the product, which initially precipitates as an oil, is obtained as a flocculent product after repeated trituration with ether and reprecipitation from methanol-ether. The resulting crude product is purified by Craig distribution over 150 stages in a mixture of methanol-buffer-chloroform-carbon tetrachloride (10:3:7:4) (buffer as under 18). The pure substance is to be found in distribution elements 75 – 112. These are combined, the organic solvents are removed in vacuo and the aqueous solution is lyophilised. The protected pentadecapeptide, which on chromatography on silica gel in the system ethyl acetate-pyridine-water (49:24:27 ) shows Rf = 0.4, is obtained.

47. Z-Gly-Phe-Gly-Pro-OtBu 15.5 g of Z-Gly-Phe-Gly-OH [manufactured according to J. R. Vaughan & J. A. Eichler, J.Am.Chem.Soc. 75, 5556 (1953)] are dissolved in 100 ml of absolute tetrahydrofurane and 5.3 ml of absolute triethylamine and 4.64 ml of isobutyl chlorocarbonate are added dropwise to the solution cooled to −20°C, whilst stirring, in such a way that the internal temperature does a way that the internal temperature does not exceed −15°C. Thereafter the mixture is allowed to react for 10 minutes at −10°C, is then again cooled to −20°C, and a solution of 7.6 g of H-Pro-OtBu in 30 ml of dimethylformamide is added dropwise whilst stirring, in such a way that the internal temperature does not exceed 0°C. The mixture is allowed to stand for 18 hours at 0°C, the triethylamine hydrochloride is then filtered off and the filtrate is evaporated at 40°C bath temperature. The residue is dissolved in 200 ml of ethyl acetate and the solution is washed with sodium bicarbonate solution, water, 10% strength tartaric acid solution and water, dried with sodium sulphate and evaporated. The residue is crystallised from ethyl acetate-petroleum ether, melting point 66°–71°C; $[\alpha]_D^{20} = -45°$ (c = 1% in chloroform).

48. Z-Gly-Phe-Gly-Pro-OH 25.6 g of Z-Gly-Phe-Gly-Pro-OtBu are dissolved in 260 ml of 90% strength trifluoracetic acid and the solution is allowed to stand for 20 minutes at 22°C. Thereafter it is concentrated in a rotational evaporator at 25°C bath temperature until it has an oily consistency; 250 ml of water are then added and the viscous mass is thoroughly kneaded at 0°C. The aqueous phase is decanted off, and the residue is washed twice more in the same manner with 100 ml of water at a time. The residue is then dried in a high vacuum at 30°C bath temperature. The residue hereupon obtained is mixed with 600 ml of ether-petroleum ether (1:1), triturated, filtered off and dried. The product is directly processed further.

49. Z-Thr(tBu)-Pro-NH$_2$ 5.27 g of Z-Thr(tBu)-OH and 1.56 g of H-Pro-NH$_2$ are dissolved in 60 ml of acetonitrile, the solution is cooled to 0°C and 3.11 g of dicyclohexylcarbodiimide are added. After 1 hour at 0°C and 20 hours at room temperature the dicyclohexylurea is filtered off and the filtrate is evaporated and the residue taken up in ethyl acetate. The ethyl acetate solution is washed with dilute citric acid solution, soda solution and water, and is dried with sodium sulphate and evaporated. On thin layer chromatography on silica gel plates the colourless residue shows $Rf_{45} = 0.76$; $Rf_{43C} = 0.70$; $Rf_{52} = 0.62$.

50. H-THr(tBu)-Pro-NH$_2$ hydrochloride 5.88 g of Z-Thr(tBu)-Pro-NH$_2$ are dissolved in 200 ml of methanol and 13.7 ml of 1 N HCl and are hydrogenated in the presence of 660 mg of palladium charcoal (10% Pd). After completion of the hydrogen uptake the mixture is evaporated to dryness at 35°C bath temperature, and dried. The residue is crystallised from ethanol-ether; melting point 170°–173°C.

51. Z-Glu(OtBu)-Thr(tBu)-Pro-NH$_2$ 3.0 g of H-Thr(tBu)-Pro-NH$_2$ hydrochloride and 4.92 g of Z-Glu(OtBu)-ONP are suspended in a mixture of 10 ml of dimethylformamide and 1.64 ml of triethylamine. The reaction mixture is stirred for 20 hours at 30°C, thereafter diluted with 150 ml of ethyl acetate, and the ethyl acetate solution is, at 0°C, washed four times with 50 ml at a time of saturated potassium carbonate solution, and with 50 ml of water, 2 × 50 ml of 5% strength citric acid solution and 2 × 50 ml of water, and is dried with sodium sulphate and evaporated. The evaporation residue is crystallised from ethyl acetate-hexane, melting point 159°–161°C.

52. H-Glu(OtBu)-Thr(tBu)-Pro-NH$_2$ 4.4 g of Z-Glu(OtBu)-Thr(tBu)-Pro-NH$_2$ are dissolved in 120 ml of methanol and hydrogenated in the presence of 1.2 g of palladium charcoal (10% Pd). After completion of the hydrogenation the catalyst is filtered off and the filtrate is evaporated, whereupon the tripeptide derivative is obtained as a crystalline crust. On thin layer chromatography on silica gel plates it shows an Rf-value = 0.50 in the system chloroform-methanol (9:1).

53. Z-Gly-Phe-Gly-Pro-Glu(OtBu)-Thr(tBu)-Pro-NH$_2$ 4.47 g of Z-Gly-Phe-Gly-Pro-OH and 3.00 g of H-Glu(OtBu)-Thr(tBu)-Pro-NH$_2$ are dissolved in 40 ml of acetonitrile and the solution is mixed with 1.76 g of dicyclohexylcarbodiimide. After 12 hours at 25°C the dicyclohexylurea which has separated out is filtered off and the filtrate is evaporated to dryness. The residue is taken up in ethyl acetate and the solution is washed with tartaric acid solution, water, sodium bicarbonate solution and water, dried over sodium sulphate and evaporated. The residue is twice reprecipitated from ethyl acetate solution by adding petroleum ether, in order to purify it. On thin layer chromatography on silica gel plates, $Rf_{43C} = 0.52$; $Rf_{52} = 0.57$.

54. H-Gly-Phe-Gly-Pro-Glu(OtBu)-Thr(tBu)-Pro-NH$_2$ 3.95 g of Z-Gly-Phe-Gly-Pro-Glu(OtBu)-Thr(tBu)-Pro-NH$_2$ are dissolved in 80 ml of methanol and the solution is hydrogenated in the presence of 600 mg of palladium charcoal (10 % Pd). After completion of the hydrogenation the catalyst is filtered off, the filtrate is evaporated to a volume of 10 ml, 20 ml of benzene are added, the mixture again concentrated to 10 ml, and the product precipitated with 70 ml of petroleum ether. The smeary precipitate is triturated to give a powder, filtered and dried; yield 3.3 g. On thin layer chromatography on silica gel plates $Rf_{43C} = 0.27$; $Rf_{52} = 0.24$; Rf in chloroform-methanol (8:2) = 0.10.

55. DPC-Met-Gly-Phe-Gly-Pro-Glu(OtBu)-Thr(tBu)-Pro-NH$_2$ 3.72 g of DPC-methionine (G.No. 17108/67, Case 6106/1–3) and 5.21 g of H-Gly-Phe-Gly-Pro-Glu(OtBu)-Thr(tBu)-Pro-NH$_2$ are suspended in 30 ml of acetonitrile and 1.98 g of dicyclohexylcarbodiimide are then added. After the air in the reaction vessel has been displaced by nitrogen, the mixture is stirred for 20 hours at 30°C. It is then diluted with 45 ml of methanol, gently warmed, and dicyclohexylurea which is still undissolved is filtered off and the filtrate is concentrated in vacuo. The residue is dissolved in ethyl acetate and washed at 0°C until neutral, as described under 52. The ethyl acetate solution on drying and evaporation leaves 9.12 g of a colourless product which crystallises from ethyl acetate-hexane; melting point 182°C. On thin layer chromatography on silica gel plates $Rf_{43C} = 0.64$, Rf in chloroform-methanol (9:1) = 0.30.

56. H-Met-Gly-Phe-Gly-Pro-Glu(OtBu)-Thr(tBu)-Pro-NH$_2$ 3.0 g of the octapeptide derivative obtained under 55 are dissolved in 35 ml of methylene chloride and mixed at room temperature with 28 ml of a mixture of monochloroacetic acid and water (3:1). After 10 minutes at room temperature the mixture is poured into 170 ml of ice-cold 2 N soda solution. The octapeptide derivative which hereupon separates out is extracted with 200 ml of n-butanol-ethyl acetate (1:1) and the organic phase is washed with water until neutral. It is then evaporated to dryness, whereupon the octapeptide derivative with a free amino group is obtained as a colourless residue which on thin layer chromatography on silica gel plates shows $Rf_{100} = 0.23$ and $Rf_{43C} = 0.51$.

57. DPl-Ser(tBu)-Ala-Tyr(tBu)-Try-Arg-Asn-Leu-Asn-Asn-Phe-His-Arg-Phe-Ser(tBu)-Gly-OH. ditosylate.

258 mg of the pentadecapeptide diacetate described under 46 are dissolved in 4 ml of absolute pyridine at 40°C and then mixed at 0°C with 1.025 ml of a 4 % strength solution of toluenesulphonic acid monohydrate (2 equivalents). The solution is evaporated to dryness in a high vacuum at 35°C bath temperature and the residue is triturated with ether. Thereafter the product is filtered off and dried (at 30°C), whereupon the ditosylate is obtained as a solid powder. $Rf_{101A}$ = 0.58; $Rf_{110}$ = 0.09; $Rf_{87}$ = 0.48.

58. DPC-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr(tBu)-Pro-NH$_2$ 254 mg of the ditosylate obtained under 57, 138 mg of H-Met-Gly-Phe-Gly-Pro-Glu(OtBu)-Thr(tBu)-Pro-NH$_2$ and 22.3 mg of N-hydroxysuccinimide are dissolved in 1 ml of dimethylformamide with warming to 60°C and the solution, cooled to 25°C, is mixed with 0.3 ml of a dimethylformamide solution containing 30 mg of dicyclohexylcarbodiimide. The reaction mixture is left under nitrogen for 4 hours at 25°C and for 12 hours at 45°C, and the dicyclohexylurea which has separated out is filtered off and the filtrate precipitated by means of a mixture of 15 ml of benzene and 40 ml of petroleum ether. The resulting precipitate is centrifuged off, dried and, after dissolving in 2.5 ml of dimethylformamide, again precipitated by adding 30 ml of benzene-petroleum ether (1:2). After decanting the solution the pecipitate is dried. Yield, 390 mg of crude product. To purify it, it is multiplicatively distributed over 200 stages in the system methanol-buffer-chloroform-carbon tetrachloride (10:3:6:5; buffer as under 18). The pure product is obtained from the elements 103 – 132 and the maximum is to be found in element 122 (K = 1.5). The yield is 213 mg; $Rf_{110}$ = 0.36; $Rf_{52A}$ = 0.25; $Rf_{96}$ = 0.42.

H-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr-(tBu)-Pro-NH$_2$ tritosylate.

210 mg of the protected tricosapeptide-amide obtained under 58) are dissolved in 10 ml of glacial acetic acid-formic acid (83 %)-water (7:1:2) and the solution is allowed to stand for 1 hour at 30°C. The product having a free α-amino group is then precipitated by adding 100 ml of ether, and centrifuged off. The supernatant material is mixed with 25 ml of petroleum ether, concentrated to a volume of 30 ml, and the precipitate thereby produced is centrifuged off. The two precipitates are combined and dissolved in 5 ml of methanol-0.1 M acetic acid (2:1). The solution is filtered through a column of Merck ion exchanger No. II in the acetate form (column 9 mm; 125 mm). The eluate is concentrated to 2 ml and then lyophilised. It is then dried to constant weight in a high vacuum at 45°C and the residue is dissolved in 10 ml of 90 % strength pyridine. 27 mg of toluenesulphonic acid monohydrate are then added and the solution is evaporated to dryness in a high vacuum. The residue is dissolved in 2 ml of water and the solution is lyophilised and thereafter dried in a high vacuum at 40°C. Hereupon 167 mg of the tritosylate of the protected tricosapeptide-amide having a free α-amino group are obtained. $Rf_{96}$ = 0.27; $Rf_{101A}$ = 0.58; $Rf_{87}$ = 0.15.

60. BOC-C̄ys-Ser(tBu)-Asn-Leu-Ser(tBu)-Thr-(tBu)-C̄ys-Val-Leu-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr-(tBu)-Pro-NH$_2$ 675 mg of BOC-C̄ys-Ser(tBu)-Asn-Leu-Ser(tBu)-Thr(tBu)-C̄ys-Val-Leu-OH, 1.30 g of the tritosylate of sequence 10 – 32 obtained under 59, 38 mg of N-methylmorpholine and 86 mg of N-hydroxysuccinimide are dissolved in 7 ml of freshly distilled dimethylformamide with warming to 70°C. The solution is then cooled to 25°C and 115 mg of dicyclohexylcarbodiimide are added. The reaction mixture is allowed to stand under nitrogen for 9 hours at 25°C and 8 hours at 45°C. Thereafter the dicyclohexylurea is filtered off and the filtrate is mixed with 80 ml of benzene and 400 ml of petroleum ether. The crude protected dotriacontapeptideamide which hereupon precipitates is dissolved in 25 ml of methanol and precipitated by adding 100 ml of benzene and 250 ml of petroleum ether. Thereafter the precipitate is filtered off and dried.

For purification, the material is subjected to a multiplicative distribution in the system methanol-buffer (as under 18)-chloroform-carbon tetrachloride (10:3:6:5) over 300 stages (phase volume: 25 ml). Control by thin layer chromatography (systems as below) shows that the fractions 101 – 130 contain the pure protected sequence 1 – 32 (maximum element 116, K = 0.63). On thin layer chromatography on silica gel, $Rf_{52}$ = 0.20; $Rf_{96}$ = 0.44; $Rf_{100}$ = 0.23; $Rf_{87}$ = 0.69; on aluminum oxide, $Rf_{45}$ = 0.67.

61. BOC-C̄ys-Ser-(tBu)-Asn-Leu-Ser(tBu)-Thr-(tBu)-C̄ys-Val-Leu-Ser(tBu)-Ala-Tyr(tBu)-Try-Arg-Asn-Leu-Asn-Asn-Phe-His-Arg-Phe-Ser(tBu)-Gly-OH 145 mg of BOC-C̄ys-Ser(tBu)-Asn-Leu-Ser(tBu)-Thr-(tBu)-C̄ys-Val-Leu-OH in 0.7 ml of degassed dimethylformamide and 0.116 ml of a molar solution of N-methylmorpholine in dimethylformamide are treated at −15°C with 0.116 ml of a molar solution of pivaloyl chloride in dimethyl formamide. The batch is allowed to stand at −10°C to −15°C for 3 minutes before a solution of 172 mg of H-Ser(tBu)-Ala-Tyr(tBu)-Try-Arg-Asn-Leu-Asn-Asn-Phe-His-Arg-Phe-Ser(tBu)-Gly-OH diacetate in 0.4 of dimethylformamide and 0.04 ml of a molar solution of N-methylmorpholine in dimethylformamide are added dropwise. The batch is allowed to stand at −5°C to −10°C for 30 minutes after which ether is added and the solid precipitate which forms is isolated. This crude product is purified by Craig distribution over 530 stages; System: methanol+λ buffer+chloroform+carbon tetrachloride (10:3:7:4) (buffer as under 18). The pure fractions (distribution coefficient: 0.9 – 0.95) are combined, the solvent evaporated under reduced pressure, and the remaining aqueous solution lyophilized. 155 mg of a white powder are obtained. $Rf_{96}$ = 0.4; $Rf_{43C}$ = 0.18.

62. BOC-C̄ys-Ser(tBu)-Asn-Leu-Ser(tBu)-Thr-(tBu)-C̄ys-Val-Leu-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr(tBu)-Pro-NH$_2$ 99 mg of BOC-C̄ys-Ser(tBu)-Asn-Leu-Ser(tBu)-Thr(tBu)-C̄ys-Val-Leu-Ser(tBu)-Ala-Tyr(tBu)-Try-Arg-Asn-Leu-Asn-Asn-Phe-His-Arg-Phe-Ser(tBu)-Gly-OH, 2HCl and 85 mg of the peptide of the sequence 25 - 32 obtained as described under 56 are treated under a current of nitrogen with 10 mg of N-hydroxysuccinimide, dissolved in 0.4 ml of dimethylformamide and stirred at 40°C until dissolution is complete. After the addition of 12.5mg of dicyclohexylcarbodiimide, dissolved in 0.1 ml of dimethylformamide, stirring is continued for 12 hours at 40°C. The crude product is precipitated with 8 ml of peroxide-free ether and centrifuged. For purification it is distributed as described under 60. The resulting product is completely identical with that described under 60).

EXAMPLE 2

H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-$NH_2$ (Thyrocalcitonin).

300 mg of BOC-Cys-Ser-Asn-Leu-Ser-Thr-Cys-Val-Leu-Ser(tBu)-Ala-Tyr-(tBu)-Try-Arg($H_2^+$)-Asn-Leu-Asn-Asn-Phe-His-Arg($H_2^+$)-Phe-Ser(tBu)-Gly-Met-Gly-Phe-Gly-Pro-Glu(OtBu)-Thr-(tBu)-Pro-$NH_2$ are hydrolysed with trifluoracetic acid as described in Example 1 in order to split off the protection groups, converted to the acetate and purified by counter-current distribution. The product proves to be identical with the dotriacontapeptide amide obtained in Example 1, according to thin layer chromatography and electrophoresis on cellulose acetate film.

The starting material can be prepared as follows

1. BOC-Val-Leu-OBzl 19.9 g (92 mmols) of BOC-Val-OH are dissolved in 200 ml of freshly distilled dimethylformamide, while heating. After cooling to 0°C, 25.9 ml of absolute triethylamine are added and the solution cooled to −10°C before 8.64 ml of chlorocarbonic acid ethyl ester are added. After 10 minutes, a solution of 23.2 g (90 mmols) of H-Leu-OBzl, HCL in 90 ml of dimethylformamide is added at −10°C. The mixture is allowed to stand at −10°C for 30 minutes, at 0°C for 3 hours, and at 20°C for 16 hours. Undissolved matter is then filtered off and the filtrate concentrated to dryness under a high vacuum. The residue is dissolved in ethyl acetate and the solution washed with dilute citric acid solution, water, sodium bicarbonate solution, and water, dried with sodium sulfate, and evaporated. On addition of petroleum ether the product crystallizes overnight. Melting point 88.5° – 89.5°C; $[\alpha]_D^{20}$ −22° (c = 2 in dimethylformamide); $Rf_2$ = 0.73.

2. H-Val-Leu-OBzl, HCl 22.8 g (54 mmols) of BOC-Val-Leu-OBzl are dissolved in 228 ml of methylene chloride. Gaseous hydrogen chloride is passed through this solution for an hour and a half. The solution is evaporated to dryness and the residue triturated three times with ether. Melting point: 192° – 195°C; $Rf_2$ = 0.27.

3. BOC-Cys(Bzl)-Va-Leu-OBzl 14.2 g (32.8 mmols) of BOC-Cys(Bzl)-ONP and 11.7 g (32.8 mmols) of H-Val-Leu-OBzl, HCl are dissolved in 137 ml of dimethylformamide, the solution is cooled to 0°C and then treated with 4.7 ml of triethylamine and 0.5 ml of glacial acetic acid. The yellow suspension is stirred at 0°C for 3 hours and at room temperature overnight. The precipitated triethylamine hydrochloride is filtered off and the filtrate evaporated to dryness under a high vacuum. The residue is dissolved in ethyl acetate and extracted twice with water, twice with 0.1N-hydrochloric acid, twice with 10% sodium chloride solution, six times with 10% sodium carbonate solution and twice with saturated sodium chloride solution. Drying over sodium sulfate is followed by evaporation to dryness. Crystallization from ethyl acetate+petroleum ether produces the protected tripeptide of melting point 113° – 115°C; $[\alpha]_D^{20}$ −33° (c = 1 in dimethylformamide). $Rf_3$ = 0.30.

4. H-Cys(Bzl)-Val-Leu-Obzl, TFA 10 g (16.3 mmols) of BOC-Cys(Bzl)-Val-Leu-OBzl are dissolved in 20 ml of 90% trifluoracetic acid and allowed to stand for 1 hour at room temperature. 200 ml of peroxide-free ether are then added and the mixture stirred for 2 hours while cooling with a mixture of ice and sodium chloride. The precipitate if filtered off and washed twice with peroxide-free ether, and dried over caustic soda under vacuum. Melting point 168° −173°C. $Rf_4$ = 0.77.

5. BOC-Ser-Thr-OBzl 9.4 (38.2 mmols) of H-Thr-OBzl, HCl and 60 ml of methylene chloride are added to a solution of 14.7 g (38.2 mmols) of BOC-Ser-OH dicyclohexylammonium salt in 100 ml of methylene chloride, and the solution is stirred for 10 minutes at room temperature, then cooled to −5°C. At this temperature, a solution of 8.0 g (38.6 mmols) of dicyclohexylcarbodiimide in 18 ml of methylene chloride is added dropwise. The batch is stirred for 3 hours at −5°C and through the whole night at room temperature. Dicyclohexylurea and dicyclohexylamine hydrochloride are filtered off and the solution then extracted by agitation three times with 0.1N-hydrochloric acid, twice with 20% sodium chloride solution, once with 10% sodium bicarbonate solution and twice with 20% sodium chloride solution, and dried over sodium sulfate. The solution is concentrated to about 100 ml, cooled to 5°C and filtered to remove more dicyclohexylurea. Evaporation to dryness produces 15.8 g of ester. For purification, the product is crystallized from ethyl acetate+hexane. Melting point 110°–111°C; $[\alpha]_D^{20}$ −8.5° (c = 2 in dimethylformamide). $Rf_2$ = 0.33.

6. H-Ser-Thr-OBzl, TFA 9.3 g (23.5 mmols) of BOC-Ser-Thr-OBzl are dissolved in 13.8 ml of 90% trifluoracetic acid and the solution allowed to stand at 22°C for 20 minutes. It is then added dropwise, while stirring, to 138 ml of dry ether, the mixture stirred for 1 hour, and allowed to stand at −10°C for 2 days. The precipitate which forms is filtered off and washed three times with dry ether, then dried over caustic soda under reduced pressure. Melting point: 128°–129°C; $Rf_7$ = 0.65; $Rf_4$ = 0.50.

7. BOC-Asn-Leu-$N_2H_2$-Z 34.8 g (150 mmols) of BOC-Asn-OH are suspended in 300 ml of acetonitrile and treated with 38 g (150 mmols) of Woodward's reagent K. While stirring and cooling, 21 ml (150 mmols of triethylamine are added dropwise in such manner that the internal temperature does not exceed +30°C. When the addition is complete, stirring is continued at 25°C for 45 minutes. To the nearly clear solution are added 52.2 g (165 mmols) of H-Leu-$N_2H_2$-Z, HCl and 23 ml (165 mmols) of triethylamine in 185 ml of acetonitrile, and the reaction mixture which soon begins to crystallize is stirred overnight at room temperature, then cooled to −10°C and stirred at that temperature for 2 hours. The crystalline precipitate is then filtered off with suction and the dipeptide derivative is washed once with cold acetonitrile, once with ethyl acetate and eight times with water until it is free of chloride. The resulting product is dried at 40°C under reduced pressure. Melting point: 194°–196°C; $[\alpha]_D^{20}$ −39° (c = 2 in dimethylformamide); $Rf_1$ = 0.45.

8. H-Asn-Leu-$N_2H_2$-Z, TFA 46.3 g (94 mmols) of BOC-Asn-Leu-$N_2H_2$-Z are dissolved in 92.6 ml of 90% trifluoracetic acid and allowed to stand at 20°C for 1 hour. The solution is then added dropwise, while stirring, into 975 ml of ether and the mixture stirred for 15 minutes. The ether is decanted from the precipitate, 210 ml of ether are added, and the whole stirred at 35°C for 1 hour under reflux, then cooled to −10°C, and the product filtered after a few hours. It is dried over caustic soda under vacuum. Melting point: 175° – 179°C; $Rf_4 = 0.46$.

9. BOC-Ser-Asn-Leu-$N_2H_2$-Z 16 g (78 mmols) of BOC-Ser-OH are dissolved in 200 ml of acetonitrile, the solution cooled to 0°C, and treated with 20 g (78 mmols) of Woodward's reagent K and 11 ml of triethylamine. The clear solution is stirred at 0°C for an hour and a half, then treated with 39.6 g (78 mmols) of H-Asn-Leu-$N_2H_2$-Z, TFA and 11 ml of triethylamine in 200 ml of dimethylformamide. The batch is stirred at room temperature overnight, then evaporated in a high vacuum at 50°C, the oily residue is taken up in 500 ml of ethylacetate, and extracted twice with 0.2N-hydrochloric acid, twice with 10% sodium chloride solution, twice with 10% sodium bicarbonate solution and twice with 10% sodium chloride solution, dried over sodium sulfate and concentrated to about 100 ml. After the addition of 20 ml of hexane, the tripeptide derivative crystallizes. Two crystallizations from ethyl acetate+10% water give unitary BOC-Ser-Asn-Leu-$N_2H_2$-Z. Melting point: 149° – 151°C; $[\alpha]_D^{20}$ −18.5° (c = 2 in dimethylformamide); $Rf_1 = 0.33$ 10. BOC-Ser-Asn-Leu-$N_2H_3$ 15.3 g (26.7 mmols) of BOC-Ser-Asn-Leu-$N_2H_2$-Z are hydrogenated in 456 ml of dimethylformamide in the presence of 2.4 g of palladium carbon (10%) at room temperature. After 5 hours the reduction is complete. The solution is filtered to remove the catalyst, then concentrated under a high vacuum. Trituration three times with ether yields a white powder. Melting point 179°–181°C; $[\alpha]_D^{20}$ −14° (c = 2 in dimethylformamide); $Rf_6 = 0.73$.

11. BOC-Ser-Asn-Leu-Ser-Thr-OBzl 8.4 g (18.7 mmols) of BOC-Ser-Asn-Leu-$N_2H_3$ in 49 ml of dimethylformamide are treated at −20°C with 19.1 ml of hydrogen chloride in tetrahydrofuran (1.97N; 37.6 mmols) and 2.53 ml of iso-amylnitrite. The batch is kept at −20°C for 8 minutes, then treated with a pre-cooled solution of 8 g (18.7 mmols) of H-Ser-Thr-OBzl, 1.13TFA and 8.3 ml of triethylamine in 49 ml of dimethylformamide. The reaction mixture is allowed to stand at 0°C for 3 days. Precipitated triethylamine hydrochloride is then filtered off, the filtrate concentrated to 40 ml in a high vacuum at 40°C, stirred while being treated with 400 ml of ethyl acetate, and kept at −10°C overnight. The precipitate is filtered off with suction and washed twice with ethyl acetate. The still moist crude product is stirred with a mixture of 60 ml of 0.03N-hydrochloric acid and 40 ml of ethyl acetate and kept at −10°C overnight. The next morning the liquid is decanted from the precipitate, the residue dissolved in aqueous actone, the acetone evaporated under a water-jet vacuum, the water-insoluble pentapeptide derivative precipitating. The precipitate is filtered off, washed with water, dried and crystallized from dimethylformamide+ethylacetate. Melting point: 207°–208°C; $[\alpha]_D^{20}$ −19.5°(c = 2 in dimethylformamide); $Rf_6 = 0.88$.

12. BOC-Ser-Asn-Leu-Ser-Thr-OH 10 g (14.1 mmols) of BOC-Ser-Asn-Leu-Ser-Thr-OBzl are hydrogenated in 300 ml of dimethylformamide at room temperature under atmospheric pressure and with the addition of 1.25 g of palladium carbon (10%). The reduction is complete at the end of 2 hours and a half. The solution is filered through asbestos to remove the catalyst, and concentrated under a high vacuum. Trituration of the residue with ether three times yields a pentapeptide which according to thin layer chromatography is unitary. Melting point, 141°–144°C; $[\alpha]_D^{20}$ −13° (c = 2 in dimethylformamide); $Rf_6 = 0.34$.

13. H-Ser-Asn-Leu-Ser-Thr-OH, TFA 8.5 g (13.7 mmols) of BOC-Ser-Asn-Leu-Ser-Thr-OH are dissolved in 85 ml of 90% trifluoracetic acid and allowed to stand at 20°C for 1 hour. The solution is then concentrated to about 25 ml, mixed with 200 ml of ether while stirring, and allowed to stand overnight at −10°C. The precipitate which forms is filtered off and stirred with another 100 ml of ether for 5 hours, then filtered off, washed twice with ether, and dried over caustic soda under vacuum. Melting point: 161°–168°C. $[\alpha]_D^{20}$ −11° (c = 2 in dimethylformamide); Rf = 0.09.

14. BOC-Cys(Bzl)-Ser-Asn-Leu-Ser-Thr-OH 5.3 g (13 mmols) of BOC-Cys(Bzl)-OSU and 7.4 g (10 mmols) of H-Ser-Asn-Leu-Ser-Thr-OH, 1.93TFA are dissolved in 75 ml of dimethylformamide. From a solution of 150 mmols of triethylamine in 100 ml of dimethylformamide, 18.1 ml (27.2 mmols) are added dropwise while stirring until the reaction mixture shows a pH of 6.4 on moist indicator paper. The solution is stirred for 3 days at room temperature, then evaporated to dryness in a high vacuum. The residue is stirred twice with 250 ml of ethyl acetate and three times with a mixture of 100 ml of ethyl acetate and 20 ml of 5% citric acid solution, filtered, and dried at 40°C under reduced pressure. Melting point: 184°–185°C; $[\alpha]_D^{20}$ −13° (c = 2 in dimethylformamide); $Rf_6 = 0.45$.

15. BOC-Cys(Bzl)-Ser-Asn-Leu-Ser-Thr-Cys(Bzl)-Val-Leu-OH 3.90 g (6 mmols) of H-Cys(Bzl)-Val-Leu-OH, 1.15TFA are dissolved in freshly distilled dimethylformamide, treated with 4.48 g (5.5 mmols) of BOC-Cys(Bzl)-Ser-Asn-Leu-Ser-Thr-OH and stirred at room temperature until all is dissolved. The solution is then cooled to 0°C, 1.26 g (11 mmols) of N-hydroxysuccinimide and 0.98 ml of triethylamine in 45 ml of dimethylformamide are added, followed by cooling to −22°C and the addition of 1.13 g (5.5 mmols) of dicyclohexylcarbodimide in 10 ml of dimethylformamide. The batch is stirred for 1 hour at −22°C, then at room temperature for 3 days, filtered to remove precipitated dicyclohexylurea, and evaporated to dryness. The residue is stirred twice with a mixture of 200 ml of ethyl acetate and 20 ml of 5% citric acid solution, then once with a mixture of 200 ml of ethyl acetate and 20 ml of 5% sodium bicabonate solution. The resulting product is filtered off and dried at 40°C in a high vacuum. Melting point: 218°–221°C; $[\alpha]_D^{20}$−28.5° (c = 2 in dimethylformamide); $Rf_8 = 0.43$.

16. BOC-Cys-Ser-Asn-Leu-Ser-Thr-Cys-Val-Leu-OH 2.5 g (1.9 mmols) of BOC-Cys(Bzl)-Ser-Asn-Leu-Ser-Thr-Cys(Bzl)-Val-Leu-OH are suspended at −40°C in 250 ml of dry, liquid ammonia. While stirring, sodium is added at the boiling point of the ammonia in such manner that the color of the reaction mixture becomes but faintly blue. After 50 minutes, all of the nonapeptide derivative is in solution. Stirring is continued for 10 minutes while maintaining the blue coloration, 1 g of ammonium chloride is added and the batch is evaporated to dryness under a pressure of about 1 mm of Hg. The residue is stirred with 30 ml of 0.1N-hydrochloric acid, the precipitate is filtered off, washed six times with water and dried. Yield: 1.38 g. The aqueous filtrate is extracted three times with ethyl acetate. The ethyl acetate extract is washed twice with 10% sodium chloride solution and once with saturated sodium chloride solution, dried over sodium sulfate, and evaporated to dryness. The product is unitary according to thin layer chromatography. $Rf_5 = 0.86$; $Rf_6 = 0.76$; $Rf_7 = 0.81$.

17. BOC-Cys-Ser-Asn-Leu-Ser-Thr-Cys-Val-Leu-OH 234 mg (0.225 mmols) of BOC-Cys-Ser-Asn-Leu-Ser-Thr-Cys-Val-Leu-OH are dissolved in 100 ml of degassed dimethylformamide and the solution treated with 1 ml of a solution containing 0.95 ml of triethylamine in 10 ml of dimethylformamide (0.675 mmols of triethylamine). At room temperature, this solution and a solution of 69.8 mg (0.248 mmols) of diiodoethane in 100 ml of degassed methanol are simultaneously dropped into a degassed mixture of 150 ml of dimethylformamide and 150 ml of methanol in the course of 90 minutes while stirring. There is added 1 ml of cyclohexane, and the batch is evaporated to dryness under a high vacuum. The residue is stirred twice with a mixture of 10 ml of 2% sodium bicarbonate and 20 ml of chloroform. The slightly yellow-colored powder is dried under a high vacuum and is revealed to be unitary by thin-layer chromatography. $Rf_5 = 0.82$; $Rf_6 = 0.75$; $Rf_7 = 0.78$.

18. BOC-Cys-Ser-Asn-Leu-Ser-Thr-Cys-Val-Leu-Ser(tBu)-Ala-Tyr(tBu)-Tyr-Arg-Asn-Leu-Asn-Asn-Phe-His-Arg-Phe-Ser(tBu)-Gly-Met-Gly-Phe-Gly-Pro-Glu(OtBu)-Thr(tBu)-Pro-NH$_2$ 412 mg of BOC-Cys-Ser-Asn-Leu-Ser-Thr-Cys-Val-Leu-OH, 360 mg of the tritosylate of the sequence 10-32 obtained as described under 59, 15 mg of N-methylmorpholine, 50 mg of N-hydroxysuccinimide, and 15 ml of dimethylformamide are stirred under nitrogen for 2 hours at 45°C. The batch is then cooled to 0°C, treated with 80 mg of dicyclohexylcarbodiimide, stirred for 2 hours at 0°C under nitrogen, treated with another 50 mg of dicyclohexylcarbodiimide, then stirred under nitrogen for 8 hours at 45°C. The batch is then poured into 100 ml of peroxide-free ether, the precipitate is filtered off with suction, washed with ether and dried at 35°C under reduced pressure. The crude product is purified by counter-current distribution as described under 60 in Example 1.

EXAMPLE 3:

N$^\alpha$-Acetyl-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-NH$_2$ (N$^\alpha$-Acetyl-Thyrocalcitonin).

1.2 g (1.2 mmol) of N$^\alpha$-Acetyl-Cys-Ser-Asn-Leu-Ser-Thr-Cys-Val-Leu-Oh are dissolved in 30 ml of freshly distilled dimethylformamide and 123 mg of N-methylmorpholine. Thereafter the solution is cooled to −15°C, 150 mg of pivaloyl chloride are added with stirring and the reaction mixture is kept for 5 minutes at −15°C. A solution, cooled to −15°C, of 2.4 g (0.9 mmol) of H-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-NH$_2$-diacetate in 50 ml of dimethylformamide 100 mg of N-methylmorpholine and water is then added dropwise. (The triacosapeptide solution is best obtained by warming the peptide in the mixture of dimethylformamide and N-methylmorpholine to 50°C under nitrogen and adding water dropwise with stirring until the peptide dissolves). After completion of the addition the mixture is left overnight under nitrogen at 0°C and is hereafter concentrated to a volume of about 30 ml in a high vacuum at 40°C bath temperature. The concentrate is poured into 500 ml of peroxide-free ether and the resulting precipitate is filtered off. The crude N$^\alpha$-acetyl-dotriacontapeptide thus obtained is purified by subjecting it to a counter-current distribution of 100 stages in the system n-butanol-glacial acetic acid-water (5 : 1 : 4). Pure N$^\alpha$-acetyl-Thyrocalcitonin is isolated from the distribution units on concentration. $Rf_{52} = 0.55$ and $Rf_{104} = 0.69$.

The nonapeptide derivative used as startin material can be pepared as follows

To 50 ml of concentrated hydrochloric acid cooled to −10°C are added 3.0g of finely powdered BOC-Cys-Ser(tBu)-Asn-Leu-Ser(tBu)-Thr(tBu)-Cys-Val-Leu-OH while stirring, the air replaced by nitrogen, and the batch allowed to stand at 0°C for 10 minutes. 250 ml of ice-water and 20 ml of glacial acetic acid are then added and the whole filtered through a column of Merck No. II weakly basic ion exchanger (acetate form). The elute is evaporated to dryness, the residue dissolved in water and lyophilized. The lyophilizate is dissolved in 40 ml of water, the pH of the solution adjusted to 6.8 by adding pyridine, the solution treated with three times its volume of dimethylformamide, After that, a solution of 600 mg of para-nitrophenylacetate in 5 ml of dimethylformamide is added and the whole is allowed to stand for 5 hours at room temperature. The batch is then evaporated to dryness at a bath temperature of 35°C and under a pressure of 0.01 mm of Hg, and then 100 ml of a 1% solution of pyridine in ether are added. The precipitated nonapeptide derivative is thoroughly triturated, filtered with suction, rinsed with ether and dried in vacuo over concentrated sulfuric acid. For purification the product is dissolved in tertiary butanol+water (3:1) and chromatographed through a column of "Sephadex" LH - 20. Fractions of 10 ml are collected and their purity checked by thin-layer chromatography on silica gel plates (system 121A); the pure fractions are combined, evaporated to dryness and dried at a bath temperature of 35°C under a pressure of 0.01 mm of Hg.

The H-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-NH$_2$ diacetate is prepared as follows 3.4 g of DPC-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr(tBu)-Pro-NH$_2$ are dissolved in 60 ml of 80% acetic acid and the solution allowed to stand at 35°C for 6 hours. It is then evaporated to dryness, the residue triturated with peroxide-free ether, the resulting powder is filtered with suction, dried, and dissolved in 50 ml of 95% trifluoroacetic acid. The solution is allowed to stand at 25°C for an hour and a half under nitrogen, then evaporated to a volume of about 5 ml, and poured into 300 ml of peroxide-free ether. The precipitate is separated by filtering with suction, washed with ether and dried over sodium hydroxide in a dessiccator. The batch is then dissolved in 10% acetic acid and the solution filtered through a column of Merck No. II ion exchanger (weakly basic, acetate form). The column is flushed with 10% acetic acid until the eluate no longer shows any absorption in the UV at 280 m/u. The eluate is then evaporated to dryness, the residue dissolved in water, and the solution lyophilized.

EXAMPLE 4

H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met(O)-Gly-Phe-Gly-Pro-Glu-Thr-Pro-NH$_2$ (Thyrocalcitonin sulphoxide).

25 mg of Thyrocalcitonine are dissolved in 5 ml of 0.05N acetic acid. 0.5 ml of 5% strength aqueous hydrogen peroxide solution are added thereto and the mixture allowed to stand for 90 minutes at room temperature. A trace of platinum black is then added and the mixture stirred until the evolution of oxygen ceases. The platinum is centrifuged off and the supernatant solution is lyophilized. The Thyrocalcitonin sulphoxide thus obtained shows $Rf_{52} = 0.51$ and $Rf_{104} = 0.48$ on thin layer chromatography on aluminium oxide. On electrophoresis on cellulose acetate (pH = 1.9; 90 minutes; 9 volts/cm) it migrates 1.5 cm towards the cathode, and on Avicel cellulose it migrates 2.9 cm.

EXAMPLE 5

N$^\alpha$-Acetyl-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met(O)-Gly-Phe-Gly-Pro-Glu-Thr-Pro-NH$_2$ (N$^\alpha$-Acetyl-Thyrocalcitonin sulphoxide).

15 mg of Thyrocalcitonin sulphoxide are dissolved in 10 ml of water and the pH is adjusted to 6.5 by adding pyridine. 4 ml of freshly prepared 0.5% strength solution of p-nitrophenyl acetate in dimethylformamide-water (1 : 3) are added to the solution and the mixture allowed to stand for 3 hours at 45°C. 1.2 ml of 5 N acetic acid are then added and the resulting p-nitrophenol and the excess p-nitrophenyl acetate are extracted with ethyl acetate. The aqueous phase is concentrated to dryness, dissolved in 3 ml of water lyophilised. The crude product thus obtained is distributed over 181 stages in a Craig distribution in the system n-butanol-glacial acetic acid-water (5 : 1 : 4; volume) using phase volumes of 3 ml each. A total of 11.5 mg of pure N$^\alpha$-acetyl-Thyrocalcitonine sulphoxide are isolated from distribution units Nos. 108 – 127 ($\mu_{max}$ = 117; K = 182) on concentrated to dryness. The substance shows the following Rf-values in a thin layer chromatogram on aluminium oxide ("Camag"): $Rf_{52} = 0.51$ and $Rf_{104} = 0.64$.

On cellulose thin layer plates ("Avicel"); $Rf_{54} = 0.61$.

In contrast to Thyrocalcitonine sulphoxide, the substance is ninhydrin-negative.

On electrophoresis on cellulose acetate strips ("Cellogel") it migrates (at pH 1.9 and 9 volts/cm) in 90 minutes 0.5 cm towards the cathode.

EXAMPLE 6

N$^\alpha$-Phenylthiocarbamoyl-H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met(O)-Gly-Phe-Gly-Pro-Glu-Thr-Pro-NH$_2$
(N$^\alpha$-Phenylthiocarbamyl-Thyrocalcitonin sulphoxide).

10 mg of Thyrocalcitonin sulphoxide are dissolved in 2 ml of pyridine-water (1:1) and allowed to react with 15 ml of phenyl isothiocyanate under nitrogen for 1½ hours at 20°C. The mixture is extracted four times with 3 ml of benzene and the aqueous solution is dried in a vacuum dessicator. The residue is dissolved in 3 ml of each of the lower and upper phase of the system n-butanol-glacial acetic acid-water (5 : 1 : 4) and purified by multiplicative distribution in the system mentioned (3 ml each of the upper and lower phase) over 177 stages. Fractions of 10 units at a time are combined, concentrated and lyophilised. 6 mg of pure N$^\alpha$-phenylthiocarbamyl-Thyrocalcitonin sulphoxide are obtained which react positively with chlorotolidine reagent, Barton's reagent and Pauly's reagent, and negatively with ninhydrin. On electrophoresis on crystalline cellulose (Avicel) the product shows a cathodic migration distance of 2.7 cm at pH 1.9 (starting product, 3.5 cm); Rf-value on Alox in the system n-butanol-glacial acetic acid-water (75 : 7.5 : 21) 0.55 (starting material 0.45), on cellulose, in the same system, 0.29 (starting material 0.20). Specific activity: 40 MRC-units/mg.

EXAMPLE 7

N$^\alpha$-Pyroglutamyl-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met(O)-Gly-Phe-Gly-Pro-Glu-Thr-Pro-NH$_2$(N$^\alpha$-Pyroglutamyl-Thyrocalciton-in sulphoxide).

15 mg of Thyrocalcitonin sulphoxide are dissolved in 1 ml of dimethylformamide, 1 ml of 0.1 % strength triethylamine in dimethylformamide (pH 6.7) and 0.3 ml of water, 2.0 mg Pyroglutamyl-2,4,5-trichlorophenyl ester are added and the mixture is allowed to stand for 72 hours at 20°C. A little water is then added and the mixture evaporated under reduced pressure and lyophilised. The residue is subjected to a multiplicative distribution in the system n-butanol-glacial acetic acid-water (4 : 1 : 5; upper and lower phase 3 ml each) over 397 stages. N$^\alpha$-Pyroglutamyl-Thyrocalcitonin sulphoxide is to be found in stages 270-345 (maximum in element 310). These fractions are combined and the solution is concentrated and lyophilised.

In a thin layer chromatogram, the resulting product shows the following Rf-Values relative to Thyrocalcitonin sulphoxide = 1.0: ps on aluminium oxide (Alox) : $Rf_{52} = 1.0 : Rf_{104} = 1.0$;
on cellulose : $Rf_{101} = 1.05 : Rf_{54} = 1.01$.

On electrophoresis, it migrates towards the cathode relative to Thyrocalcitonin sulphoxide = 1.0:
on Cellogel, pH 1.9, 140 volt: 0.39,
on Selecta cellulose, pH 1.9, 140 volt, 0.81.

EXAMPLE 8

H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-OH 25 mg of BOC-Cys-Ser(tBu)-Asn-Leu-Ser(tBu)-Thr(tBu)-Cys-Val-Leu-Ser(tBu)-Ala-Try(tBu)-Try-Arg-Asn-Leu-Asn-Asn-Phe-His-Arg-Phe-Ser(tBu)-Gly-Met-Gly-Phe-Gly-Pro-Glu(OtBu)-Thr-(tBu)-Pro-OtBu are kept at room temperature for one hour in 2 ml of 95% trifluoracetic acid. The batch is then poured into 20 ml of deep-cooled, peroxide-free ether, filtered and washed with some ether, and the solution of the filter residue in a small amount of water is run over a small column of Amberlite CG-45 in the acetate form. The result is observed by means of a UV cell, and the fractions containing the product are lyophilized. Thin-layer chromatogram on alumina:
$Rf_{45} = 0.36$; $Rf_{52} = 0.39$; $Rf_{79} = 0.42$.

Electrophoreses: On Selecta plates (pH = 1.9, 1½ hours, 280 V) distance traveled towards the cathode, 6.3 cm; on cellogel (pH = 1.9, 1½ hours, 280 V) distance traveled towards the cathode, 4.3 cm.

The starting material can be prepared as follows

1. Z-Thr(tBu)-Pro-OtBu

To a solution of 6.3 g of Z-Thr(tBu)-OH and 2.34 ml of N-methylmorpholine in 100 ml of tetrahydrofuran are added at −17°C 3.0 ml of chloroformic acid-isobutylester, the batch stirred for 20 minutes at this temperature, then reacted with 6.7 g of H-Pro-OtBu in 100 ml of tetrahydrofuran. The batch is allowed to stand at room temperature overnight, then filtered, the filtrate evaporated to dryness under vacuum, the residue dissolved in ethyl acetate and extracted several times with dilute aqueous citric acid solution, dilute aqueous sodium carbonate solution, and saturated sodium chloride solution. The resulting oily compound shows in the thin-layer chromatogram on silica gel:

$Rf_{43C} = 0.89$; $Rf_{45} = 0.75$; $Rf_{52} = 0.64$. $[\alpha]_D^{20} = -44° \pm 1°$ [c = 1.0 in EtOH]

2. H-Thr(tBu)-Pro-OtBu, HCl 2.7 g of Z-Thr(tBu)-Pro-OtBu are decarbobenzoxylated with hydrogen in 200 ml of methanol with the addition of 2.9 ml of aqueous 2N-hydrochloric acid and 500mg of palladium carbon catalyst (10% Pd) in a shaking flask under atmospheric pressure at room temperature. When hydrogen is no longer being absorbed, the batch is filtered and evaporated to dryness and the product crystallized. Melting point: 142° − 145°C (with decomposition). Thin-layer chromatogram on silica gel:

$Rf_{43C} = 0.45$; $Rf_{45} = 0.70$; $Rf_{52} = 0.55$ $[\alpha]_D^{20} -66° \pm 0.5°$ [c = 2.2 in EtOH]

3. Z-Glu(OtBu)-Thr(tBu)-Pro-(OtBu)

7.79 g of H-Thr(tBu)-Pro-OtBu, HCl and 9.79 g of Z-Glu(OtBu)-ONP are dissolved together in 15 ml of dimethylformamide, the solution treated with 3.2 ml of triethylamine, and stirred overnight at 27° − 30°C. The solution is evaporated to dryness under vacuum, the residue dissolved in ethyl acetate and chloroform and the solution extracted by agitation with citric acid, sodium carbonate solution, and sodium chloride solution as described under 1, above. The resulting crude product is chromatographed on silica gel. The product can be eluted with hexane×ether (1:1) and ether. It crystallizes from a mixture of ether and hexane. Melting point: 135° − 137°C. Thin-layer chromatogram on silica gel:

$Rf_{CHCl_3-MeOH(95:5)} = 0.53$; $Rf_{CHCl_3-acetone(1:1)} = 0.72$; $Rf_{45} = 0.82$ $[\alpha]_D^{20} = 44° \pm 0.5°$ [c = 2 in EtOH].

4. H-Glu(OtBu)-Thr(tBu)-Pro-OtBu 777 mg of the compound described under 3 are hydrogenated in 250 ml of methanol with 300 mg of 10% palladium catalyst on carbon. A viscous oil is obtained which can be used for the next stage without prior purification.

Thin-layer chromatogram on silica gel: $Rf_{CHCl_3/MeOH(9:1)} = 0.48$; $Rf_{43A} = 0.50$.

5. Z-Gly-Phe-Gly-Pro-Glu(OtBu)-Thr(tBu)-Pro-OtBu 667 mg of Z-Gly-Phe-Gly-Pro-OH are dissolved in 20 ml of acetonitrile together with 608 mg of H-Glu(OtBu)-Thr(tBu)-Pro-OtBu obtained under 4 and after the addition of 222 mg of N-hydroxysuccinimide and 269 mg of dicyclohexylcarbodiimide, stirred for 16 hours at room temperature. The precipitated dicyclohexyl urea is filtered off, the filtrate evaporated, the residue dissolved in much ethyl acetate and the solution washed as described under 1, above. After drying and evaporation of the solution in vacuo, the crude product is purified by chromatography on a column of silica gel. It can be eluted with ethyl acetate an ethyl acetate×ethanol (4:1). It is then reprecipitated from ether. Melting point: 96° − 99°C. Thin-layer chromatogram on silica gel: $Rf_{CHCl_3-MeOH(9:1)} = 0.40$; $Rf_{102A} = 0.75$; $Rf_{52} = 0.80$ 6. H-Gly-Phe-Gly-Pro-Glu(OtBu)-Thr(tBu)-Pro-OtBu 858 mg of Z-Gly-Phe-Gly-Pro-Glu(OtBu)-Thr(tBu)-Pro-OtBu are hydrogenated in 150 ml of methanol in the presence of 200 mg of palladium-carbon catalyst (10% Pd). The product is triturated with ether×hexane (1:1) to form an amorphous powder. In the thin-layer chromatogram on silica gel it shows the following values:

$Rf_{CHCl_3-MeOH(9:1)} = 0.16$; $Rf_{102E} = 0.17$; $Rf_{52} = 0.41$

7. DPC-Met-Gly-Phe-Gly-Pro-Glu(OtBu)-Thr(tBu)-Pro-OtBu 410 mg of DPC-Met-OH are stirred at room temperature for 19 hours with 750 mg of H-Gly-Phe-Gly-Pro-Glu(OtBu)-Thr(tBu)-Pro-OtBu in 15 ml of acetonitrile under nitrogen with the addition of 152 mg of N-hydroxysuccinimide and 271 mg of dicyclohexylcarbodiimide. The dicyclohexylurea is filtered off, the filtrate evaporated under vacuum, the residue dissolved in much ethyl acetate and the solution washed as described under 1. above, then evaporated. The crude product is purified by chromatography through a column of silica gel. It can be eluted with ethyl acetate×ethanol (4:1).

Thin-layer chromatogram on silica gel: $Rf_{CHCl_3-MeOH(9:1)} = 0.42$; $Rf_{102E} = 0.39$; $Rf_{53} = 0.29$.

8. H-Met-Gly-Phe-Gly-Pro-Glu(OtBu)-Thr(tBu)-Pro-OtBu 190 mg of the DPC compound obtained under 7 are dissolved in 3 ml of methylene chloride under nitrogen and treated with 2.9 ml of a 3:1 mixture of monochloracetic acid and water. After a reaction period of 12 minutes at room temperature the batch is poured into 20 ml of ice-cold 2N-aqueous sodium carbonate solution which is then extracted with 3 × 30 ml of n-butanol+ethylacetate (1:1). The extract is washed until neutral with a saturated aqueous sodium chloride solution, dried and evaporated, and the residue extracted several times with ether. The extraction residue, an amorphous powder, exhibits the following Rf values in thin-layer chromatography on silica gel: $Rf_{43C} = 0.31$; $Rf_{52} = 0.30$; $Rf_{100} = 0.27$ 9. BOC-C$\overset{\frown}{y}$s-Ser(tBu)-Asn-Leu-Ser(tBu)-Thr(tBu)-C$\overset{\smile}{y}$s-Val-Leu-Ser(tBu)-Ala-Tyr(tBu)-Try-Arg-Asn-Leu-Asn-Asn-Phe-His-Arg-Phe-Ser(tBu)-Gly-Met-Gly-Phe-Gly-Pro-Glu(OtBu)-Thr(tBu)-Pro-OtBu 55 mg of BOC-C$\overset{\frown}{y}$s-Ser(tBu)-Asn-Leu-Ser(tBu)-Thr(tBu)-C$\overset{\smile}{y}$s-Val-Leu-Ser(tBu)-Ala-Try(tBu)Try-Arg-Asn-Leu-Asn-Asn-Phe-His-Arg-Phe-Ser(tBu)-Gly-OH-ditosylate are stirred at 40°C with 81 mg of H-Met-Gly-Phe-Gly-Pro-Glu(OtBu)-Thr(tBu)-Pro-OtBu in 0.2 ml of dimethylformamide and 9 mg of N-hydroxysuccinimide while introducing nitrogen. When all has dissolved, 7.3 mg of dicyclohexylcarbodiimide in 1 ml of dimethylformamide are added and the whole is stirred for 22 hours at 40°C. After cooling, the product is precipitated with 8 ml of peroxide-free ether and centrifuged. The crude product is distributed multiplicatively in the system methanol+buffer+λ chloroform+carbon tetrachloride (10:3:6:5) over 100 stages (K = 0.4). (Buffer, see Example 1 under 18) The contents of the tubes containing the product are poured together, evaporated, and the ammonium acetate expelled under a high vacuum at 40°C. $Rf_{52A} = 0.24$; $Rf_{100} = 0.25$; $Rf_{110} = 0.65$ on silica gel plates.

EXAMPLE 9

A 5 ml-dry ampoule is prepared containing

| | |
|---|---|
| lyophilised synthetic Thyrocalcitonin | 0.5 mg |
| mannitol | 20 mg |

For subcutaneous injection the contents of the dry ampoule are dissolved in 0.1-molar acetate buffer of pH 4.6 (mixture of sodium acetate and acetic acid). The preparation is administered, for instance, once a day.

We claim:
1. A peptide of the formula I

H-L-Cys-L-Ser-L-X-L-Leu-L-Ser-L-Thr-L-Cys-L-Val-L-Leu-L-Ser-L-Ala-L-Tyr-L-Arg-L-X-Leu-L-X-L-X-L-Phe-L-His-L-Arg-L-Phe-L-Ser-Gly-L-Z-Gly-L-Phe-Gly-L-Pro-L-Y-L-Thr-L-Pro-NH$_2$ in which X is a member selected from the group consisting of aspartyl and asparaginyl, Y is a member selected from the group consisting of glutamyl and glutaminyl and Z is a member selected from the group consisting of methionyl, valyl, norvalyl, leucyl, isoleucyl, and norleucyl, a Met$^{25}$-sulfoxide, N$^\alpha$-acyl derivative or N$^\alpha$-desamino derivative thereof with the exception of H-Cys-Ser-Asn-Leu-Ser-Thr-Cys-Val-Leu-Ser-Ala-Tyr-Try-Arg-Asn-Leu-Asn-Asn-Phe-His-Arg-Phe-Ser-Gly-Met-Gly-Phe-Gly-Pro-Glu-Thr-Pro-NH$_2$ and its Met$^{25}$-sulfoxide, or a therapeutically acceptable acid addition salt thereof.

\* \* \* \* \*